United States Patent
Hannewald et al.

(10) Patent No.: US 10,426,717 B2
(45) Date of Patent: Oct. 1, 2019

(54) GLYCOL ESTERS OF DICAFFEOYLQUINIC ACID AND USES THEREOF

(71) Applicant: PLANT ADVANCED TECHNOLOGIES PAT, Vandoeuvre-les-Nancy (FR)

(72) Inventors: Paul Hannewald, Vandoeuvre-les-Nancy (FR); Frédéric Bourgaud, Vandoeuvre-les-Nancy (FR); Benoît Mignard, Toulouse (FR); Damien Boeglin, Vandoeuvre-les-Nancy (FR)

(73) Assignee: PLANT ADVANCED TECHNOLOGIES PAT, Vandoeuvre-les-Nancy (FR)

(*) Notice: Subject to any disclaimer, the term of this patent is extended or adjusted under 35 U.S.C. 154(b) by 0 days.

(21) Appl. No.: 16/073,036

(22) PCT Filed: Jan. 27, 2017

(86) PCT No.: PCT/EP2017/051749
§ 371 (c)(1),
(2) Date: Oct. 18, 2018

(87) PCT Pub. No.: WO2017/129734
PCT Pub. Date: Aug. 3, 2017

(65) Prior Publication Data
US 2019/0038533 A1    Feb. 7, 2019

(30) Foreign Application Priority Data

Jan. 29, 2016  (FR) ....................... 16 50745
Oct. 26, 2016  (FR) ....................... 16 60402

(51) Int. Cl.

| | |
|---|---|
| *A61K 8/37* | (2006.01) |
| *A61Q 19/08* | (2006.01) |
| *A61K 8/97* | (2017.01) |
| *A61K 36/39* | (2006.01) |
| *C07C 39/17* | (2006.01) |
| *C07C 69/757* | (2006.01) |
| *A61K 8/9783* | (2017.01) |
| *A61K 8/39* | (2006.01) |

(52) U.S. Cl.
CPC ............ *A61K 8/375* (2013.01); *A61K 8/39* (2013.01); *A61K 8/97* (2013.01); *A61K 8/9783* (2017.08); *A61K 36/39* (2013.01); *A61Q 19/08* (2013.01); *C07C 39/17* (2013.01); *C07C 69/757* (2013.01); *A61K 2236/00* (2013.01); *C07C 2601/14* (2017.05)

(58) Field of Classification Search
None
See application file for complete search history.

(56) References Cited

U.S. PATENT DOCUMENTS

| | | | |
|---|---|---|---|
| 7,350,331 B1 | 4/2008 | Gontier et al. | |
| 2004/0170581 A1 | 9/2004 | Henry et al. | |

FOREIGN PATENT DOCUMENTS

| | | |
|---|---|---|
| EP | 1260212 A1 | 11/2002 |
| JP | 2012041297 A | 3/2012 |
| JP | 2015199674 A | 11/2015 |
| WO | 0133942 A1 | 5/2001 |
| WO | 2006014028 A1 | 2/2006 |

OTHER PUBLICATIONS

International Search Report, dated Apr. 20, 2017, from corresponding International Application No. PCT/EP2017/051749.
Kim, Hyoung-Ja, Chang-Bae Jin, and Yong-Sup Lee. "Isolation and antioxidative activities of caffeoylquinic acid derivatives and flavonoid glycosides from leaves of sweet potato (*Ipomoea batatas* L.)." Biomolecules & Therapeutics 15, No. 1 (2007): 46-51. English language summary/abstract.
Rattan, Suresh IS. "The future of aging interventions: aging intervention, prevention, and therapy through hormesis." The Journals of Gerontology Series A: Biological Sciences and Medical Sciences 59, No. 7 (2004): B705-B709.

*Primary Examiner* — Craig D Ricci
(74) *Attorney, Agent, or Firm* — Young & Thompson

(57) ABSTRACT

Disclosed are glycol esters of dicaffeoylquinic acids, in particular dipropylene glycol esters of dicaffeoylquinic acids (DPG esters of DCQ) and propane-1.3-diol esters of dicaffeoylquinic acids of general formula:

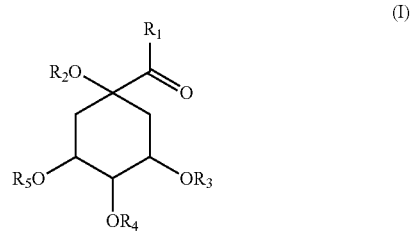

(I)

wherein $R_1$ is a dipropylene glycol radical or a propane 1,3 diol radical, and any two of the radicals $R_2$, $R_3$, $R_4$ and $R_5$ are a caffeoyl group, the other two being a hydrogen atom. Also disclosed is a plant extract including same, the method for preparing same and a cosmetic composition including the compounds or extracts, intended for preventing or delaying the appearance of skin ageing effects.

5 Claims, 6 Drawing Sheets

GLYCOL ESTERS OF DICAFFEOYLQUINIC ACID AND USES THEREOF

FIELD OF THE INVENTION

The present invention relates to dicaffeoylquinic acid glycol esters, in particular dicaffeoylquinic acid dipropylene glycol esters and propane 1,3 diol esters, and their use as active principles in cosmetic compositions. The present invention relates in particular to the use as an active principle of dicaffeoylquinic acid glycol dipropylene esters (DCQ-DPG esters) and dicaffeoylquinic acid propane 1,3 diol esters in a cosmetic composition for mitigating or delaying the appearance of signs of intrinsic or extrinsic skin ageing, and a skin cosmetic care process using such a cosmetic composition.

PRIOR ART

Skin is the first barrier of human body. It protects organs from temperature, moisture differences, and aggressions from the external environment, as UV rays or pollutant agents. It also has an important role in homeostasis, for example to regulate body temperature. However, excessive chemical and physical stimulations (sun, light or UV exposure; stress and malnutrition) deteriorate normal skin functions and induce ageing thereof. This so-called "extrinsic" ageing causes clinic alterations such as deep wrinkles and the formation of a skin that lost firmness, suppleness and elasticity thereof. These transformations are essentially due to histopathologic changes, such as an excessive modification of the elastic tissue in the upper dermis and a quantitative and qualitative degeneration of collagen fibres.

Concomitantly, the so-called "intrinsic", "physiological", "normal" or "chronobiological" ageing, is the consequence of a programmed senescence where endogenous factors operate. This intrinsic ageing causes in particular a slowing down in the renewal of skin cells, that is keratinocytes, which essentially results in the appearance of clinic alterations such as the reduction in the subcutaneous fatty tissue and the appearance of fine lines, and histopathologic changes such as an increase in the number and thickness of elastic fibres, a loss of vertical fibres of the elastic tissue membrane, and the presence of large uneven fibroblasts in the cells of this elastic tissue. The present invention is concerned with both intrinsic and extrinsic types of ageing.

The search for new molecules or active ingredients usable in cosmetics is necessary to be able to develop efficient products to give a younger aspect to skin, mitigate wrinkles, smooth skin and restore radiance. Therefore, laboratories compete with each other in innovation looking for increasingly elaborate actives.

Several categories of anti-ageing active principles are now marketed:
- anti-oxidant agents (vitamins A, C, E, trace elements, plants, algae) fight against free radicals, improve skin relief and repair damages caused by pollution. More particularly, retinol, the active form of vitamin A, smoothes shallow fine lines and increases skin thickness by stimulating cell renewal,
- alpha hydroxyacids (AHAs), present in citrus fruits, grape and sugar cane, benefit from an exfoliating capacity which removes dead cells from the epidermis, moisturises and smoothes the features to receive radiance,
- new formulations also enable collagen and elastin production to be stimulated, tissue regeneration by "laser" and "botox-like" cares to be promoted inspired by botulinum toxin to mitigate feature contraction.

Patent application US 2004/0170581 describes a chicory extract comprising DCQs as well as the use of such an extract for its anti-age activity. It is set out that chicory extract combined with retinoic acid stimulates the enzymatic activity of glucose-6-phosphate dehydrogenase which is involved in the fight against free radicals and thus against ageing. Thus, according to document US 2004/0170581, a chicory extract comprising DCQs has a strong potential in fighting against oxidative stress and ageing, and is involved in the renewal of skin vital components, such as collagen, elastin and glycoproteins.

Skin ageing causes many histopathologic changes, modifying beauty and visual skin quality; actually, it can induce a decrease in moisturising, a modification of epidermis keratinocyte differentiation, and a slowing down in their proliferation. The active ingredients and mechanisms described above make it possible in some extent to repair, a posteriori, ageing-related skin alterations. However, there is a need for preventing ageing, in particular by delaying signs of intrinsic or extrinsic skin ageing.

Oxidative stress (in the form of UV radiations, pollution or free radicals) is today recognised as one of the main determinants involved in ageing phenomena (F. J. Kelly. *Occup. Environ. Med.*, 2003, 60: 612-616). Ageing would thus be related to a progressive and irreversible build-up of damages caused by oxidative stress because of the decrease with age in the defence system activity (Kevin C. Kregel, Hannah J. Zhang. *Am J Physiol Regul Integr Comp Physiol*, 2007, 292:$R$18-$R$36). Actives enabling either of these defence mechanisms to be enhanced have thus very interesting potential anti-age preventive effects.

A hormetic agent, or hormetin, is a molecule or treatment generating a low intensity stress, without significant cellular damage, but which induces a protective and antioxidant response in order to ensure cell homeostasis. The hormetic effect, or hormesis, is thus a positive stimulation of the organism defence mechanisms by applying light to moderate stresses. This stimulation thus improves functional capacities of adjustment, maintenance and repair mechanisms, and can thus have a variety of anti-age effects (Suresh I. S. Rattan. *The Journals of Gerontology Series A: Biological Sciences and Medical Sciences*, 2004, 59:B705-B709). The hormetic effect can be represented as a training and a preparation of cells to oxidative stress. Thereby, the organism is better able to respond by limiting as much as possible the damage undergone upon subsequent exposure to these stresses. The use of hormetic agents, or hormetins, thus has an established effect in preventing and thus delaying ageing by activating cell defence mechanisms (Zsolt Radak, Hae Young Chung, Sataro Goto. *Biogerontology*, 2005, 6: 71-75).

To be referred to as a hormetin, a substance has to induce a defensive cellular response in particular by modifying the expression of some genes, called vitagenes (S. I. Rattan. *Ann. N. Y. Acad. Sci.* 1998, 854: 54-60), in which there are in particular genes coding for Heme-Oxygenase 1 (D. Gems, L. Partridge. *Cell Metabolism*, 2008, 7: 200-204). Thus, fighting against ageing and anti-age effect depend on the efficiency of the cellular maintenance and repair systems. Among these systems, there are in particular oxidative stress defence proteins such as Heme-oxygenase 1 (HO-1) or heat shock protein 70 (HSP70).

Protein HO-1 (coded by the HMOX gene) is involved in heme degradation and is known to demonstrate a protective role against oxidative stress (Morse and Choi, 2005; Vile et al., 1994). The gene is induced soon after free radical exposure, and its protective role is essentially due to its capacity to degrade heme (having pro-oxidising properties) into carbon monoxide and biliverdin, a precursor of a powerful antioxidant metabolite, bilirubin.

On the other hand, HMOX (gene coding for HO-1) is a target gene of the transcription factor Nrf2. The antioxidant response of the transcription factor Nrf2 is thus considered as "the primary cellular defence against oxidative stress cytotoxic effects". Nrf2 activation results in the induction of many cytoprotective proteins, that is HO-1, but also HSP70, NAD(P)H, glutamate cysteine ligase, glutathione S transferase pi, UDP-glucuronosyltransferase 1A6 and inhibition of nitric oxide synthase. All the proteins induced are proteins having cytoprotective actions. Thus, protein HSP70 (coded by the HSPA1A gene) is a heat shock protein induced in case of stress and exerting a protective action on other proteins (Murphy, 2013). It also controls essential mediators of the apoptic machinery. NAD(P)H dehydrogenase, a quinone 1 encoded by the NQO1 gene exerts in turn, a detoxifying action by allowing formation of hydroquinones from quinones, preventing radical species from being formed. It is also induced in response to a cellular stress (UV, heavy metals, pro-oxidant agents, etc.) (Nguyen et al., 2009). Glutamate cysteine ligase (coded by the GCLM gene), and glutathione S transferase pi (coded by the GSTP1 gene) are involved in glutathione synthesis and in its conjugation to endogenous or exogenous substances respectively for restoring the cell redox status (Lu et al., 2009; Strange et al., 2001). UDP-glucuronosyltransferase 1A6 (coded by the UGT1A6 gene) induces the conjugation of glucuronic acid to other endo- or xeno-biotic substances in order to facilitate the excretion thereof (Buckley & Klaassen, 2009). Finally, nitric oxide synthase (coded by the NOS2 gene) is involved in the production of reactive nitrogen species (RNS) that can be produced during an oxidative stress. The activation of the Nrf-2 dependent pathway decreases the induction of the NOS2 gene resulting from a stress (Petri et al., 2012) and thus the production of these reactive nitrogen species. Nrf-2 induction, resulting in inducing the HMOX, HSPA1A, NQO1, GCLM, GSTP1, and UGT1A6 genes, and in inhibiting the NOS2 gene, thereby contributes to the cell hormetic response.

By way of example, the best documented molecular hormetins are curcumin and ferulic acid, the application of which on human fibroblasts results in generating a free radical overproduction, inducing some protective or anti-oxidant enzymes such as HSP70 or HO-1, and triggering an overall anti-oxidant response via the Nrf-2 dependent signalling pathway (Lima et al., *Mol. Nutr. Food Res.*, 54, 1-13, 2010; Calabrese et al., *Clinics in Dermatology*, 26, 358-363, 2008).

However, there is a need for new hormetic substances, capable of having a role in preventing ageing. In particular skin ageing, which can be easily obtained, and which fulfil the current consumer interest towards plant origin ingredients.

SUMMARY OF THE INVENTION

Within the scope of the invention, it has been discovered that a plant extract comprising dicaffeoylquinic acid glycol esters, in particular DCQ DPG esters and DCQ propane 1,3 diol esters, has a hormetic effect on fibroblasts and can thus be used in anti-age cosmetic applications. More precisely, the inventors have shown that the DCQ DPG esters present in this extract have a hormetic effect on fibroblasts, unlike DCQs themselves, which have not this activity. The inventors have also shown that DCQ glycol esters, in particular DCQ DPG esters and DCQ propane 1,3 diol esters, present in a plant extract, significantly modify the expression of genes implied in an oxidative stress, skin pigmentation and dermo-epidermal junction in cellular cultures of human fibroblasts or melanised and reconstituted human epidermis.

In a first aspect, the present invention thus relates to a dicaffeoylquinic acid glycol ester compound having the general formula (I):

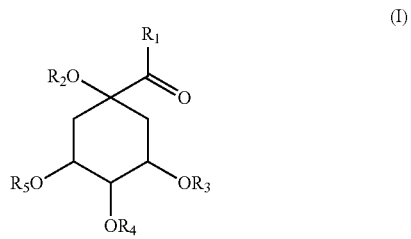

wherein $R_1$ represents a radical chosen from the group consisting of the radicals of the following formulae (IIa) to (IIe), (III), (IVa) to (IVb) and (Va) to (Vd):

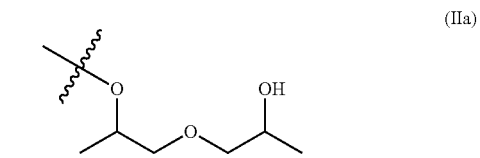

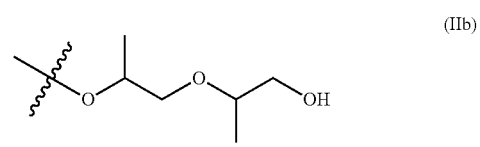

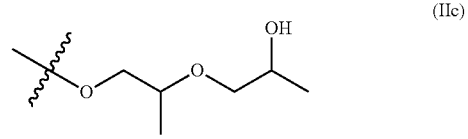

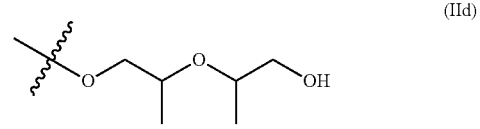

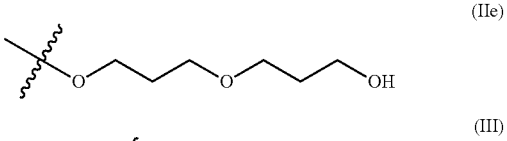

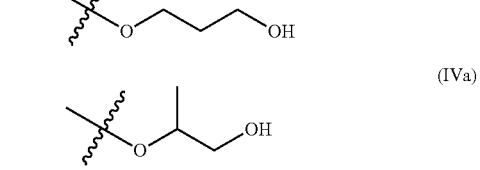

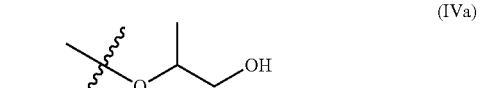

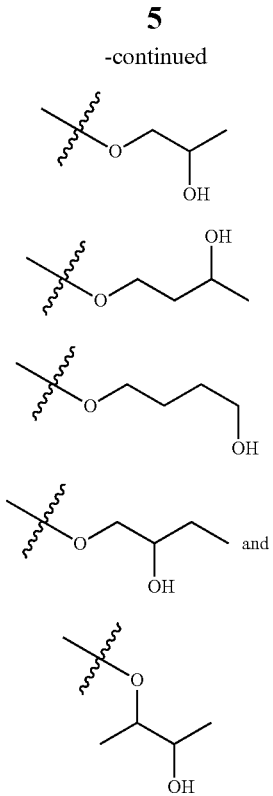

any two of the radicals $R_2$, $R_3$, $R_4$ and $R_5$ represent a caffeoyl group, the other two representing a hydrogen atom.

In a second aspect, the invention relates to a plant extract comprising at least one compound according to the invention.

In a third aspect, the invention relates to a process for preparing said plant extract comprising at least one compound according to the invention, comprising the following steps:
a) culturing plants synthesising dicaffeoylquinic acids (DCQ),
b) solid/liquid extraction of plants from step a) in glycol or in a glycol solution.

In a fourth aspect, the present invention relates to an extract likely to be obtained by said process according to the invention.

In another aspect, the present invention relates to a cosmetic composition comprising as an active agent, at least one compound according to the invention or a plant extract according to the invention, and advantageously an excipient.

In yet another aspect, the invention relates to the use as a cosmetic agent of at least one compound according to the invention or of a plant extract according to the invention or of a cosmetic composition according to the invention.

The present invention also relates to a skin cosmetic care method for preventing or delaying the appearance of skin ageing effects, characterised in that it comprises applying, on at least one body or face skin part, the cosmetic composition according to the invention.

$0.01 < p < 0.05$; **: $0.001 < p < 0.01$). The values $p < 0.05$ have been considered as significant, the values $0.001 < p < 0.01$ as highly significant and the values $p < 0.001$ as very highly significant.

Figure 6:
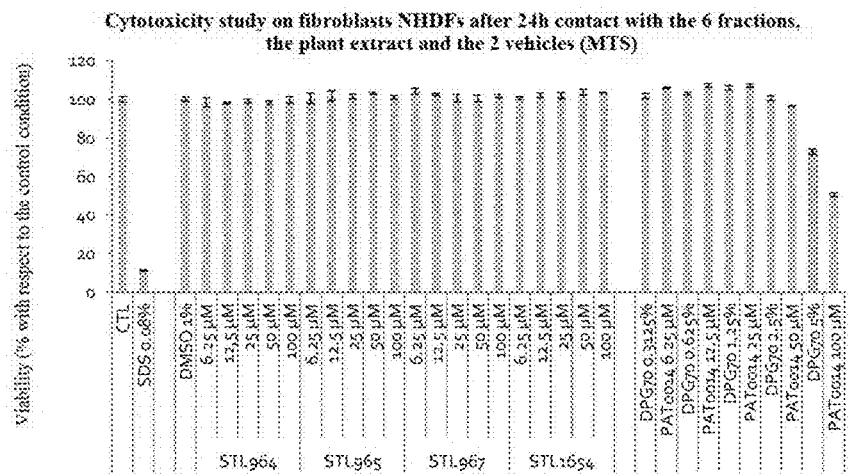

FIG. 6. Measurements of the viability of fibroblasts NHDFs after 24h treatment with different concentrations of fractions and vehicles. The viability percentages have been calculated with respect to the untreated control (CTL) set to 100%. The fractions STL964 (mainly comprising 3,4-DCQ), STL 965 (mainly comprising 3,5-DCQ), STL 967 (mainly comprising 4,5-DCQ) and STL 1654 (mainly comprising DCQ DPG esters), have been prepared in DMSO (dimethylsulfoxide). The PAT0014 extract corresponds to an *Ipomoea batatas* extract according to the invention prepared in DPG70 (70% v/v Dipropylene glycol in water).

Figure 7:
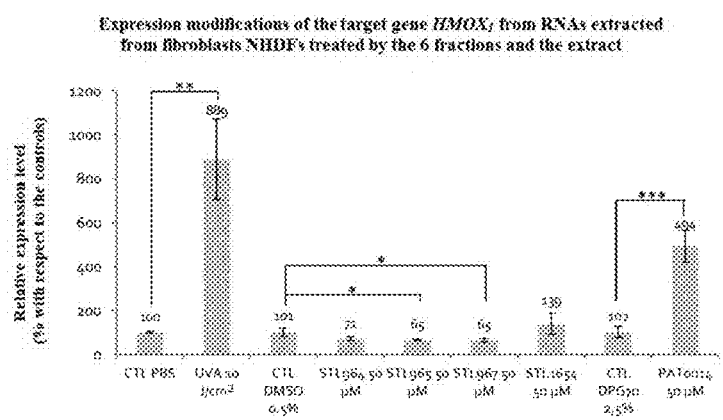

FIG. 7. Expression level of the HMOX1 gene in the fibroblasts NHDFs treated for 24 h by PBS ("CTL PBS" control), DMSO ("CTL DMSO" control), the fractions STL 964 (mainly comprising DCQ isomers), STL 965 (mainly comprising 3,5-DCQ), STL 967 (mainly comprising DCQ isomers) and STL 1654 (mainly comprising DCQ DPG esters), 70% v/v DPG in water ("CTL DPG70" control) or by the extract PAT0014 (corresponding to an extract according to the invention) or in UVA-irradiated fibroblasts NHDFs, after 6 h of recovery. The fractions STL 964, STL 965, STL 967 and STL 1654 being prepared in DMSO, their control fraction is "CTL DMSO". Likewise, the extract PAT0014 is prepared in 70% DPG, its control fraction thus corresponding to "CTL DPG70". The results are expressed in relative percentage with respect to the respective controls. The statistical analysis made is based on a student t-test individually comparing each treatment with its control (*: $p < 0.05$; : $0.001 < p < 0.01$ and *: $p < 0.001$). The values $p < 0.05$ have been considered as significant, the values $0.001 < p < 0.01$ as highly significant and the values $p < 0.001$ as very highly significant.

Figure 8:
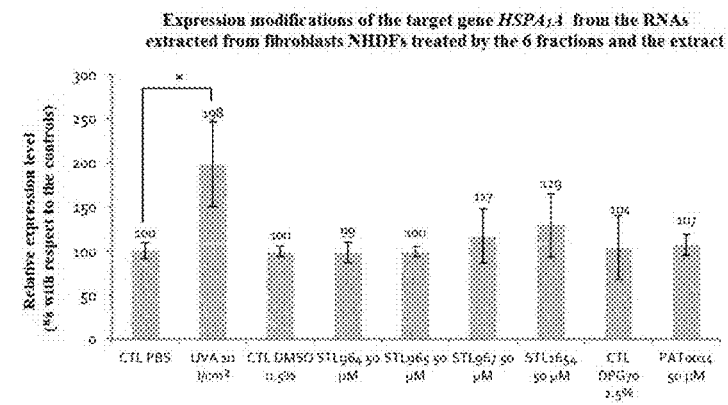

FIG. 8. Expression level of the HSPA1A gene in fibroblasts NHDFs treated for 24 h by PBS ("CTL PBS" control), DMSO ("CTL DMSO" control), the fractions STL 964 (mainly comprising 3,4-DCQ), STL 965 (mainly comprising 3,5-DCQ), STL 967 (mainly comprising 4,5-DCQ) and STL 1654 (mainly comprising DCQ DPG esters), 70% v/v DPG in water ("CTL DPG70" control) or by the extract PAT0014 (corresponding to an extract according to the invention) or in UVA-irradiated fibroblasts NHDFs, after 6 h of recovery. The fractions STL 964, STL 965, STL 967 and STL 1654 being prepared in DMSO, their control fraction is "CTL DMSO". Likewise, the extract PAT0014 is prepared in 70% DPG, its control fraction thus corresponding to "CTL DPG70". The results are expressed in relative percentage with respect to the respective controls. The statistical analysis made is based on a student t-test individually comparing each treatment with its control (*: $p < 0.05$; : $0.001 < p < 0.01$ and *: $p < 0.001$). The values $p < 0.05$ have been considered as significant, the values $0.001 < p < 0.01$ as highly significant and the values $p < 0.001$ as very highly significant.

Figure 9:
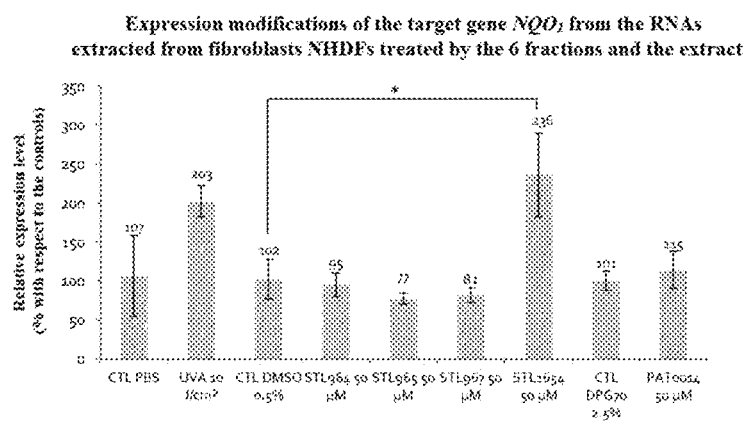

FIG. 9. Expression level of the NQO1 gene in fibroblasts NHDFs treated for 24 h by PBS ("CTL PBS" control), DMSO ("CTL DMSO" control), the fractions STL 964 (mainly comprising 3,4-DCQ), STL 965 (mainly comprising 3,5-DCQ), STL 967 (mainly comprising 4,5-DCQ) and STL 1654 (mainly comprising DCQ DPG esters), 70% v/v DPG in water ("CTL DPG70" control) or by the extract PAT0014 (corresponding to an extract according to the invention) or in UVA-irradiated fibroblasts NHDFs, after 6 h of recovery. The fractions STL 964, STL 965, STL 967 and STL 1654 being prepared in DMSO, their control fraction is "CTL DMSO". Likewise, the extract PAT0014 is prepared in 70% DPG, its control fraction thus corresponding to "CTL DPG70". The results are expressed in relative percentage with respect to the respective controls. The statistical analysis made is based on a student t-test individually comparing each treatment with its control (*: $p < 0.05$; : $0.001 < p < 0.01$ and *: $p < 0.001$). The values $p < 0.05$ have been considered as significant, the values $0.001 < p < 0.01$ as highly significant and the values $p < 0.001$ as very highly significant.

Figure 10:
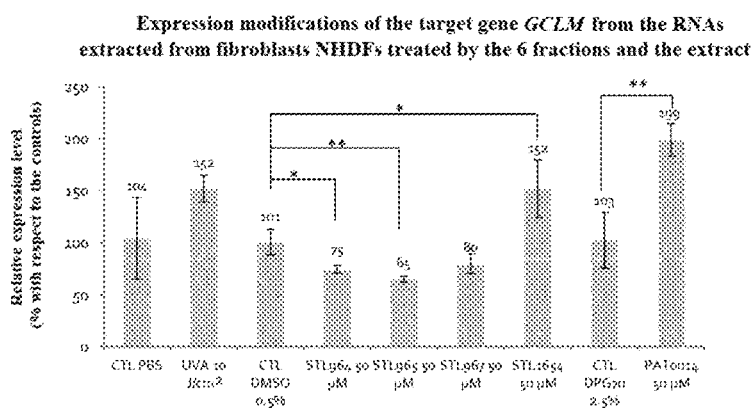

FIG. 10. Expression level of the GCLM gene in fibroblasts NHDFs treated for 24 h by PBS ("CTL PBS" control), DMSO ("CTL DMSO" control), the fractions STL 964 (mainly comprising 3,4-DCQ), STL 965 (mainly comprising 3,5-DCQ), STL 967 (mainly comprising 4,5-DCQ) and STL 1654 (mainly comprising DCQ DPG esters), 70% v/v DPG in water ("CTL DPG70" control) or by the extract PAT0014 (corresponding to an extract according to the invention) or in UVA-irradiated fibroblasts NHDFs, after 6 h of recovery. The fractions STL 964, STL 965, STL 967 and STL 1654 being prepared in DMSO, their control fraction is "CTL DMSO". Likewise, the extract PAT0014 is prepared in 70% DPG, its control fraction thus corresponding to "CTL DPG70". The results are expressed in relative percentage with respect to the respective controls. The statistical analysis made is based on a student t-test individually comparing each treatment with its control (*: $p < 0.05$; : $0.001 < p < 0.01$ and *: $p < 0.001$). The values $p < 0.05$ have been considered as significant, the values $0.001 < p < 0.01$ as highly significant and the values $p < 0.001$ as very highly significant.

Figure 11:
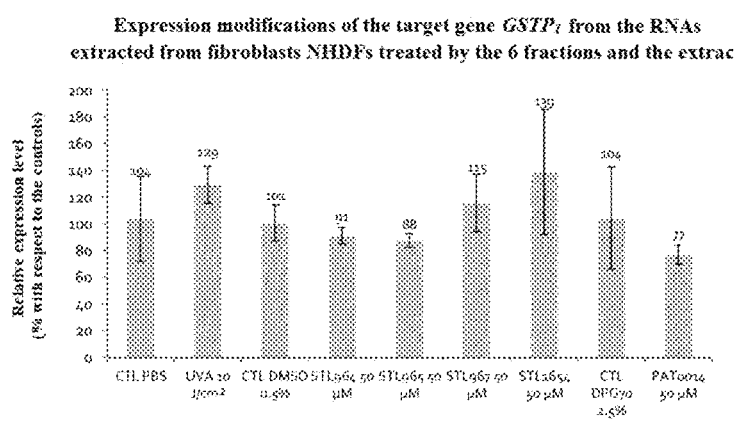

FIG. 11. Expression level of the GSTP1 gene in fibroblasts NHDFs treated for 24 h by PBS ("CTL PBS" control), DMSO ("CTL DMSO" control), the fractions STL 964 (mainly comprising 3,4-DCQ), STL 965 (mainly comprising 3,5-DCQ), STL 967 (mainly comprising 4,5-DCQ) and STL 1654 (mainly comprising DCQ DPG esters), 70% v/v DPG in water ("CTL DPG70" control) or by the extract PAT0014 (corresponding to an extract according to the invention) or in UVA-irradiated fibroblasts NHDFs, after 6 h of recovery. The fractions STL 964, STL 965, STL 967 and STL 1654 being prepared in DMSO, their control fraction is "CTL DMSO". Likewise, the extract PAT0014 is prepared in 70% DPG, its control fraction thus corresponding to "CTL DPG70". The results are expressed in relative percentage with respect to the respective controls. The statistical analysis made is based on a student t-test individually comparing each treatment with its control (*: $p < 0.05$; : $0.001 < p < 0.01$ and *: $p < 0.001$). The values $p < 0.05$ have been considered as significant, the values $0.001 < p < 0.01$ as highly significant and the values $p < 0.001$ as very highly significant.

DETAILED DESCRIPTION OF THE INVENTION

Definitions

By "glycol" it is meant a diol in which the two hydroxyl groups are carried by different carbons. In the present description, the term "glycol" designates pure glycol at 100% or in solution, in particular in aqueous solution, wherein said glycol is present in an amount of 10% to 99%, more particularly between 40% and 90%, and further more particularly between 50% and 75%.

According to a particular aspect, glycol being pure or in solution, in particular an aqueous solution, is characterised by an acidic pH, in particular when it is used in a solid/liquid extraction step. According to a particular aspect, said glycol used during a solid/liquid extraction step is characterised by a pH between 0.8 and 5, preferably between 0.8 and 3, more preferentially between 0.8 and 2.2. According to another particular aspect, a plant extract according to the invention is characterised by a pH between 2.5 and 5, preferably between 2.9 and 4.4.

More particularly, said glycol is chosen from the following group: dipropylene glycol, propane 1,3 diol, propane 1,2 diol and butylene glycol.

By "dipropylene glycol" (abbreviated as "DPG" throughout the present description), it is meant a mixture of the four following isomeric chemical compounds: 1-1'-oxydipropan-2-ol of the formula (VIa), 2-(2-hydroxypropoxy)propan-1-ol of the formula (VIb), 2-2'-oxydipropan-1-ol of the formula (VIc) and 1,1'oxy-dipropan-3-ol of the formula (VId):

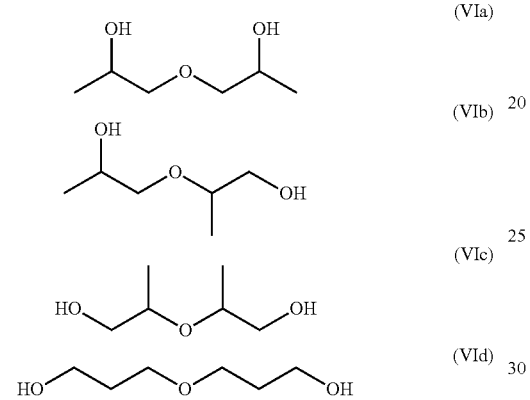

According to the present invention, the compounds of the formulae (VIa), (VIb), (VIc) and (VId), as described above, correspond to the different radicals from the four dipropylene glycol isomers. More particularly, the radical of the formula (IIa) comes from the isomer of the formula (VIa), the radicals of the respective formulae (IIb) and (IIc) come from the same isomer of the formula (VIb) and differ in the position of the hydroxyl which is grafted to the compound of the general formula (I), the radical of the formula (IId) comes from the isomer of the formula (VIc) and the radical of the formula (IIe) comes from the isomer of the formula (VId).

By "propanediol", it is meant propane 1,3 diol and propane 1,2 diol. Propane 1,3 diol, or trimethylene glycol, has the following formula (VII):

$$HO\diagup\diagdown OH. \quad (VII)$$

Said propane 1,3 diol can be prepared by chemical synthesis according to techniques known to those skilled in the art and described in the literature, it is also commercially available. Said propane 1,3 diol can also be produced by implementing a fermentation process under suitable conditions of a living organism, in particular an *Escherichia coli* genetically modified strain. The propane 1,3 diol thus obtained is designated by the term "biosourced propane 1,3 diol", such a product is produced and then purified as described in particular in the international application WO 2004/101479 and marketed as Zemea®.

According to the present invention, the compound of the formula (III) as described above corresponds to the radical from propane 1,3 diol of the formula (VII).

"Propane 1,2 diol", or propylene glycol, has the following formula (VIII):

$$\text{(VIII)}$$

According to the present invention, the compounds of the formulae (IVa) and (IVb) as described above correspond to the radical from propane 1,2 diol of the formula (VIII).

By "butylene glycol", it is meant butane 1,2 diol of the formula (IXa), butane 1,3 diol of the formula (IXb), butane 2,3 diol of the formula (IXc) and butane 1,4 diol of the formula (IXd), illustrated below:

(IXa), (IXb), (IXc), (IXd)

According to the present invention, the compounds of the formulae (Va), (Vb), (Vc) and (Vd) as described above correspond to the radicals from the 4 butylene glycol isomers: butane 1,2 diol (IXa), butane 1,3 diol (IXb), butane 2,3 diol (IXc) and butane 1,4 diol (IXd).

By "dicaffeoylquinic acid" (abbreviated as "DCQ" throughout the present description), it is meant a diester comprised of a quinic acid molecule two of the four alcohol functions of which have been esterified by a caffeic acid molecule. DCQs thus are acids of the following general formula (X):

(X)

wherein $R_2$, $R_3$, $R_4$ and $R_5$ are as defined in the formula (I) described above (i.e. any two of the radicals $R_2$, $R_3$, $R_4$ and $R_5$ represent a caffeoyl group, the other two representing a hydrogen atom).

The different DCQ isomers are thus acids of the general formula (X), with $R_2$, $R_3$, $R_4$ and $R_5$ as defined in the table 1 below.

TABLE 1

| Dicaffeoylquinic acids (DCQs) | $R_2$ | $R_3$ | $R_4$ | $R_5$ |
|---|---|---|---|---|
| Structure of dicaffeoylquinic acids. | | | | |
| 1,3-dicaffeoylquinic (1,3-DCQ) | Caffeoyl | Caffeoyl | H | H |
| 1,4-dicaffeoylquinic (1,4-DCQ) | Caffeoyl | H | Caffeoyl | H |
| 1,5-dicaffeoylquinic (1,5-DCQ) | Caffeoyl | H | H | Caffeoyl |
| 3,4-dicaffeoylquinic (3,4-DCQ) also called isochlorogenic acid B | H | Caffeoyl | Caffeoyl | H |
| 3,5-dicaffeoylquinic (3,5-DCQ) also called isochlorogenic acid A | H | Caffeoyl | H | Caffeoyl |
| 4,5-O-dicaffeoylquinic (4,5-DCQ) also called isochlorogenic acid C | H | H | Caffeoyl | Caffeoyl |

By "caffeoyl group", it is meant a radical of the general formula (XI), from caffeic acid:

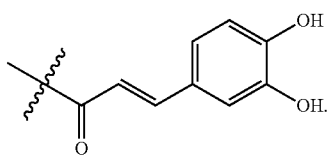

(XI)

By "chlorogenic acid", it is meant the simple caffeic acid and quinic acid ester, also called trans-5-O-caffeoyl-D-quinate, of the formula (XII):

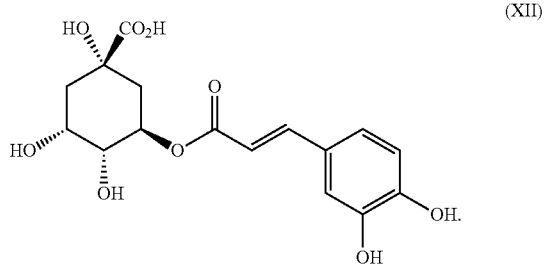 [SMILES: O=C(/C=C/c1ccc(O)c(O)c1)O[C@@H]1C[C@](O)(C(=O)O)C[C@@H](O)[C@H]1O]

(XII)

By "DCQ synthesising plants", it is meant any plant naturally containing, in one or more of its parts, at least one DCQ. Among the plants known to contain DCQs, those of the following families: Apiaceae (in particular *Foeniculum vulgare*), Aquifoliaceae (in particular *Ilex* species), Araliaceae (in particular *Cynara* species, *Inula* species, *Artemisia* species, *Achillea millefolium*, *Taraxacum officinale*, *Echinacea angustifolia*, *Helianthus annuus*, *Smallanthus sonchifolius*, *Gynura divaricata*, *Echinops galalensis*, *Tanacetum vulgare*, and *Youngia japonica*), Caprifoliaceae (in particular *Lonicera* species and *Knautia arvensis*), Convoivuiaceae (in particular *Ipomoea* species, *Convolvulus* species, *Cressa cretica* and *Cuscuta japonica*), Fabaceae, Rosaceae, Rubiaceae (in particular *Coffea* species and *Machaonia brasiliensis*), and Solanaceae (in particular *Solanum* species) can be mentioned.

By "part" of a plant, it is meant any constituent part of a plant such as the roots, stem, leaves, fruit, skin, grains or kernel.

Within the scope of the present invention, by "solid/liquid extraction", it is meant any solvent extraction technique which consists in extracting a chemical species being in a solid and being soluble in said solvent. Among these solid/liquid extraction techniques, maceration, root exudation, infusion, decoction, extraction by Soxhlet and Kumagawa extractors, microwave-assisted extraction, ultrasound-assisted extraction, enzymatic extraction, and supercritical fluid extraction (CO2+DPG).

Within the scope of the invention, by "plant cultivation under above-ground conditions", it is meant any cultivation mode in which the plant roots are not in the ground. More precisely, the above-ground cultivation is a cultivation in which the roots of the plants rest on a reconstituted, off ground medium. This cultivation medium is regularly irrigated by nutrient solutions suitable for the plant cultivated.

There are different above-ground cultivation techniques such as substrateless systems which require an oxygen enriched nutrient solution, and systems with a substrate. Among the substrateless systems, aquiculture for which the nutrient solution is non-circulating and is contained in the cultivation bench, Nutrient Film Technique (N.F.T.) for which the nutrient solution is enriched with dissolved oxygen during its movement by air exchange, and aeroponics for which the plant roots are in contact neither with a solid medium, nor with a liquid medium: they are supplied with a nutrient spray obtained by fogging (via a fogger) of the nutrient solution in a closed medium. Among the systems with a substrate, there is sub-irrigation in which the nutrient solution penetrates the substrate at its lower part and percolation in which the nutrient solution is distributed by batch irrigation at the upper surface of the system and then percolates downwardly of the substrate. The mineral or organic substrate is neutral and inert like sand, clay or rock wool for example. This substrate can also of industrial origin.

By "root exudation", it is meant the recovery of metabolites contained in plant roots by means of a liquid contacted by percolation, sprinkling or dipping with the roots still attached to the living plant or freshly cut (for less than 24 hours, and preferably as soon as possible after cutting, ideally right after cutting). In particular, root exudation can be made using a step of macerating roots from the plants, freshly cut and/or still attached to the living plant, in an appropriate solvent and for an appropriate duration.

Within the scope of the invention, by "root exudation in a solvent", it is meant a root exudation as defined above by which the liquid contacted with the roots is a solvent, said solvent is advantageously a glycol chosen among: dipropylene glycol, propane 1,3 diol, propane 1, 2 diol and butylene glycol or a solution containing said glycol.

Dicaffeoylquinic Acid Glycol Esters

The present invention thus relates to compounds, being dicaffeoylquinic acid glycol esters, and in particular dicaffeoylquinic acid dipropylene glycol esters and dicaffeoylquinic acid propanediol esters, of the general formula (I):

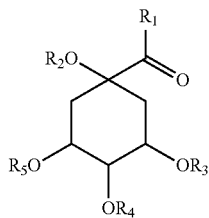
(I)

in which

R₁ represents one of the radicals of the following formula (IIa), (IIb), (IIc), (IId), (IIe), (III), (IVa), (IVb), (Va) (Vb), (Vc) or (Vd):

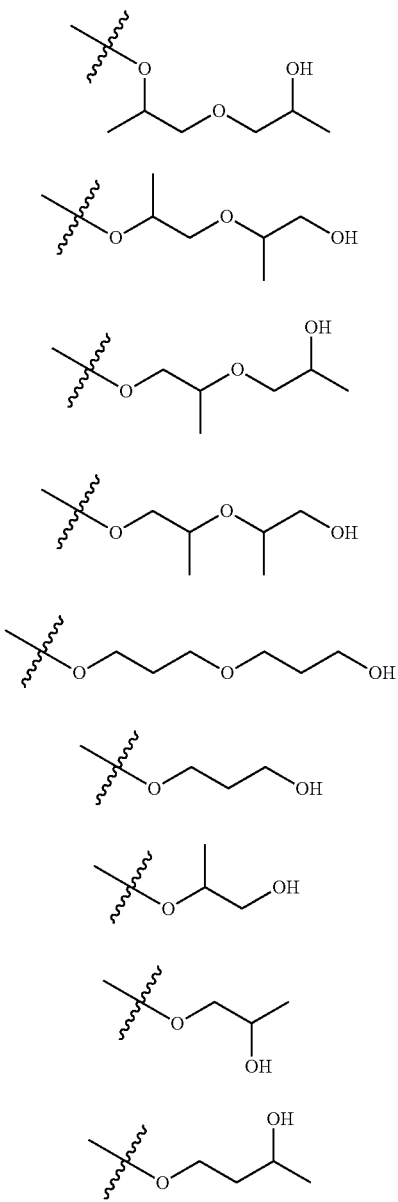

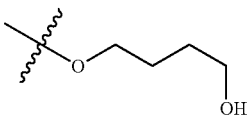
(Vb)

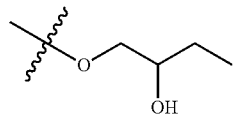
(Vc)

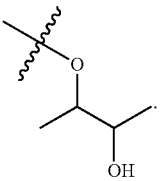
(Vd)

And any two of the radicals $R_2$, $R_3$, $R_4$ and $R_5$ represent a caffeoyl group, the other two representing a hydrogen atom.

Among the compounds of the formula (I) according to the present invention, glycol esters, in particular DPG esters and propanediol esters of:

1,3-dicaffeoylquinic acid,
1,4-dicaffeoylquinic acid,
1,5-dicaffeoylquinic acid,
3,4-dicaffeoylquinic acid,
3,5-dicaffeoylquinic acid, and
4,5-dicaffeoylquinic acid can be mentioned.

Advantageously, the compounds of the general formula (I) according to the invention are characterised in that $R_2$ represents a hydrogen atom. Thus, among the advantageous compounds of the present invention, glycol esters, in particular DPG esters and propanediol esters of:

3,4-dicaffeoylquinic acid,
3,5-dicaffeoylquinic acid, and
4,5-dicaffeoylquinic acid can be mentioned.

Advantageously, compounds of the general formula (I) according to the invention are characterised in that $R_2$ and $R_4$ represent a hydrogen atom. Compounds of the general formula (I) according to the invention which are particularly advantageous are those characterised in that $R_2$ and $R_4$ represent a hydrogen atom and $R_3$ and $R_5$ represent a caffeoyl group, thus corresponding to 3,5-dicaffeoylquinic acid glycol esters, and in particular to 3,5-dicaffeoylquinic (3,5-DCQ) acid DPG esters and to 3,5-dicaffeoylquinic acid propanediol esters.

Still further advantageously, according to a first aspect, the glycol ester compounds according to the invention are 3,5-DCQ DPG esters and are selected from the molecules of the following respective formulae (Ia), (Ib), (Ic), (Id) and (Ie):

(Ia)

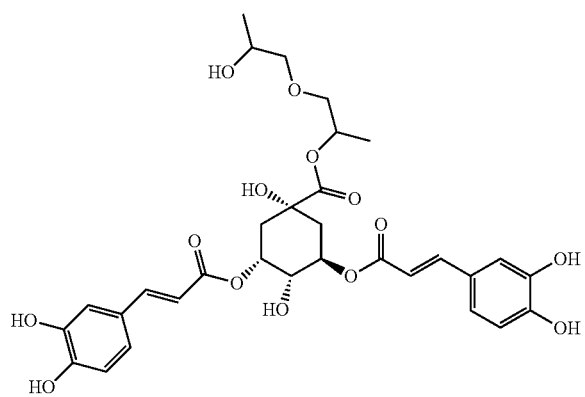

(Ib)

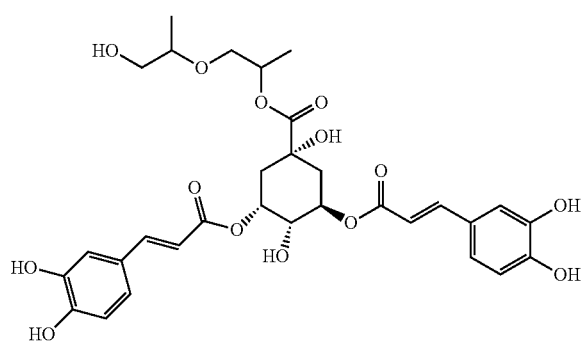

(Ic)

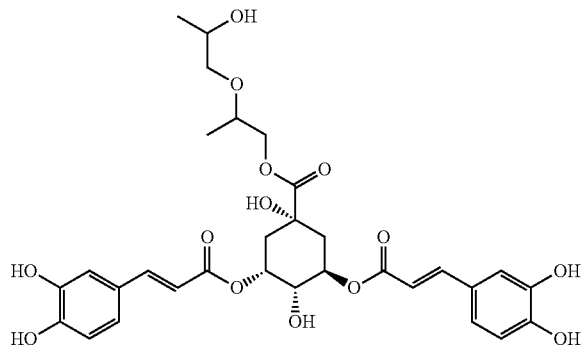

(Id)

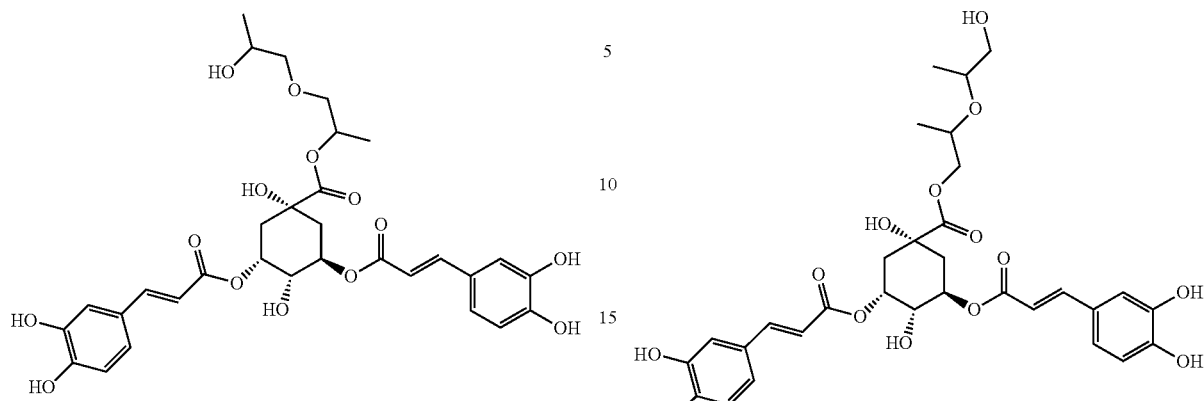

(Ie)

According to this aspect, the compounds according to the invention come from the esterification of 3,5-dicaffeoylquinic acid and dipropylene glycol (DPG).

According to a second advantageous aspect, the compound 3,5-DCQ propane 1,3 diol ester according to the invention has the following formula (If):

(If)

According to this aspect, the compounds according to the invention come from the esterification of 3,5-dicaffeoylquinic acid and propane 1,3 diol, in particular biosourced propane 1,3 diol.

According to a third advantageous aspect, the compound 3,5-DCQ propylene glycol ester according to the invention is selected from the molecules of the following formulae (Ig) and (Ih):

(Ig)

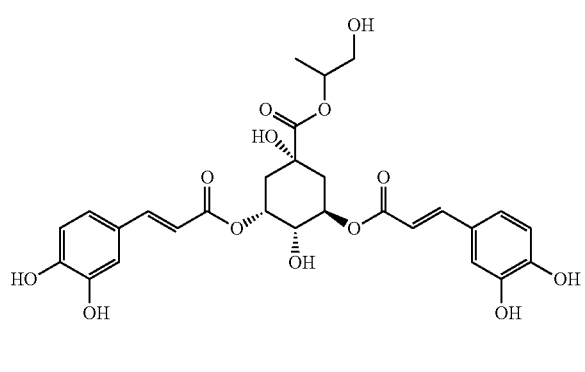

(Ih)

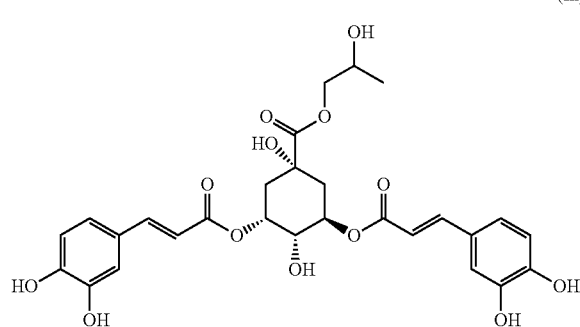

According to this aspect, the compounds according to the invention come from the esterification of 3,5-dicaffeoylquinic acid and propylene glycol.

According to a fourth advantageous aspect, the compound 3,5-DCQ butanediol ester according to the invention is selected from the molecules of the following formulae (Ii), (Ij), (Ik) and (Il):

(Ii)

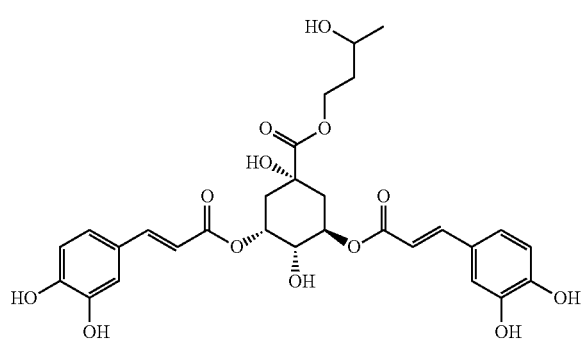

(Ij)

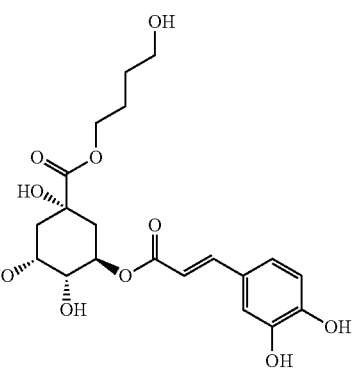

(Ik)

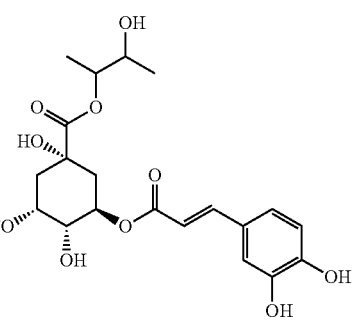

(Il)

According to this aspect, the compounds according to the invention come from the esterification of 3,5-dicaffeoylquinic acid and butylene glycol.

This esterification can be achieved by chemical synthesis, in particular according to the reaction scheme below for dipropylene glycol (DPG) and propane 1,3 diol:

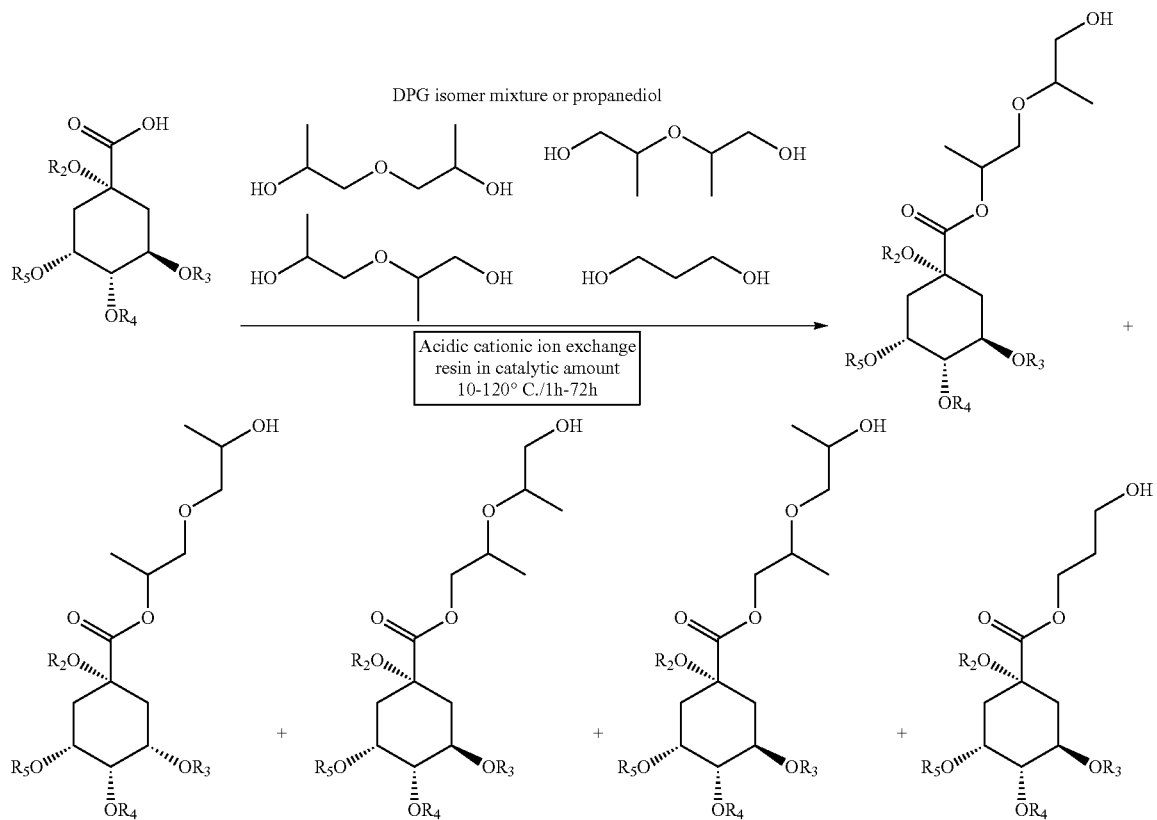

$R_2$, $R_3$, $R_4$ and $R_5$ are as defined in the formula (I) described above (i.e. any two of the radicals $R_2$, $R_3$, $R_4$ and $R_5$ represent a caffeoyl group, the other two representing a hydrogen atom).

In this embodiment, the DCQ(s) can be of natural origin, the DCQ glycol esters, in particular the DCQ DPG esters or DCQ propane 1,3 diol esters, being consequently obtained by hemisynthesis.

In a preferred aspect, the compounds according to the present invention are obtained by plant extraction of DCQ synthesising plants, or particularly DCQ rich plants, in glycol or in an aqueous glycol solution, said glycol being chosen from: dipropylene glycol, propane 1,3 diol, propane 1,2 diol and butylene glycol.

By "plant extraction", it is meant any extraction process known to those skilled in the art, advantageously a solid/liquid extraction of one or several parts of a DCQ synthesising plant in glycol or in an aqueous glycol solution, said glycol being chosen from: dipropylene glycol, propane 1,3 diol, propane 1,2 diol and butylene glycol. At the end of the extraction, liquid/liquid extraction, purification, concentration, clarifying filtration and/or discoloration steps can advantageously enable the compounds according to the invention or a plant extract concentrated in compounds according to the invention to be obtained. All these techniques are described in the literature and are known to those skilled in the art.

Plant Extract Comprising at Least One of the Glycol Esters, in Particular a DCQ DPG Ester or a DCQ Propane 1,3-diol Ester The inventors have found that plant extracts of DCQ synthesising plants obtained by extracting said plants in glycol, or in a glycol solution, in particular dipropylene glycol or propane 1,3 diol, comprise compounds according to the invention and have a hormetic effect.

In a second aspect, the present invention thus relates to a plant extract comprising at least one compound of the general formula (I) according to the present invention.

More particularly, the present invention relates to a plant extract comprising at least one compound of the general formula (I) according to the invention, said plant being selected from one or several part(s) (in particular the roots) of a DCQ synthesising plant as defined above, in particular Ipomoea species, and in particular The Ipomoea batatas species.

The present invention thus relates in particular to an Ipomoea batatas extract comprising at least one compound according to the invention, and in particular an Ipomoea batatas root extract comprising at least one compound according to the invention.

Further, because the plants used for obtaining a plant extract according to the invention are particularly DCQ rich and that the DCQ esterification from glycol or an aqueous glycol solution, in particular from DPG or propane 1,3 diol, or an aqueous DPG or propane 1,3 diol solution, can in some embodiments be partial, the plant extract according to the invention comprising at least one compound according to the invention can also comprise a dicaffeoylquinic acid (DCQ) and/or a chlorogenic acid.

In one embodiment, the present invention thus relates to a plant extract comprising at least one compound according to the present invention, and a dicaffeoylquinic acid and/or a chlorogenic acid.

The plant extract according to the present invention can in particular comprise at least one compound according to the present invention and at least one of the following compounds: 3,5-di-caffeoylquinic acid, 3,4-di-caffeoylquinic acid and 4,5-di-caffeoylquinic acid.

According to this aspect, a plant extract according to the invention is an *Ipomoea batatas* root extract comprising at least one compound according to the invention, in particular a DCQ glycol ester, and comprising an amount of DCQ glycol ester between 70 and 1 400 mg/L, expressed as mg ester or acid per volume of plant extract.

The plant extract according to the invention is advantageously an *Ipomoea batatas* root extract comprising at least one compound according to the invention and having the composition given in the following Table 2:

TABLE 2

Composition of an *Ipomoea batatas* root extract according to the invention

| Compounds present | Content (mg/L) |
| --- | --- |
| 3,4-DCQ/Isochlorogenic acid B | 50-150 |
| 3,5-DCQ/Isochlorogenic acid A | 600-1200 |
| 4,5-DCQ/Isochlorogenic acid C | 100-200 |
| 3,5 DCQ DPG esters | 80-240 |

According to another aspect, the plant extract according to the invention is advantageously an *Ipomoea batatas* root extract comprising at least one compound according to the invention and comprising an amount of 3,5-DCQ propane 1,3 diol ester between 700 and 1 400 mg/L.

According to a particular aspect, one object of the invention is a plant extract, in particular a root extract, more particularly chosen from:
an extract obtained by root exudation in a solvent,
an extract obtained by root maceration in a solvent, and
a mixture of at least one extract obtained by root exudation in a first solvent and of at least one extract obtained by root maceration in a second solvent.

In accordance with the invention, said solvent is either pure glycol, or an aqueous glycol solution; in the case of a mixture of root extracts, said first and second solvents can be identical or different; in accordance with the invention, the solvents used for root exudation and maceration are chosen from: dipropylene glycol, propane 1,2 diol, propane 1,3 diol and butylene glycol.

According to a particular aspect, one object of the invention is an *Ipomoea batatas* extract, in particular a root *Ipomoea batatas* extract, more particularly chosen from:
an *Ipomoea batatas* extract obtained by root exudation in a solvent, preferably dipropylene glycol, the root exudation step being preferably made on roots attached to the plant,
an *Ipomoea batatas* extract obtained by root maceration in a solvent, preferably dipropylene glycol, the root maceration step being made preferably on cut and possibly dried roots,
an *Ipomoea batatas* extract obtained by root maceration in a solvent, preferably propane diol, more preferentially propane 1,3 diol, the root maceration step being preferably made on cut and possibly dried roots, and
a mixture comprising an *Ipomoea batatas* extract obtained by root exudation in dipropylene glycol and an *Ipomoea batatas* extract obtained by root maceration in dipropylene glycol, and possibly an
*Ipomoea batatas* extract obtained by root maceration in propane 1,3 diol.

Process for Preparing a Plant Extract According to the Invention and Extract Likely to be Obtained by Said Process The plant extract according to the invention can be obtained by solid/liquid extraction of DCQ synthesising plants in glycol or an aqueous glycol solution, in particular dipropylene glycol or propane 1,3 diol as a solvent, according to different protocols known to those skilled in the art.

According to a third aspect, the present invention thus relates to a process for preparing a plant extract according to the invention.

Said process according to the invention advantageously comprises a step of solid/liquid extraction of a plant or of at least one part (in particular roots) of a DCQ synthesising plant (in particular of *Ipomoea batatas*) in glycol, in particular in dipropylene glycol or propane 1,3 diol.

Advantageously, the plant extract according to the invention is prepared according to a preparation process comprising the following steps of:
a) culturing plants synthesising at least one dicaffeoylquinic acid, and in particular *Ipomoea batatas*
b) solid/liquid extraction of the plants from step a) in a solvent chosen from: dipropylene glycol, propane 1,3 diol, propane 1,2 diol and butylene glycol.

According to a particular aspect of the process according to the invention, the solid/liquid extraction step is made by implementing a process chosen from: root exudation and root maceration.

Preferably, in a process according to the invention, root exudation is made on roots still attached to the plant or freshly cut. According to another preferred aspect, the root maceration is made on cut and possibly dried roots. Drying the roots can be made by implementing any suitable drying process, known to those skilled in the art, and in particular by placing the roots at a temperature between 40° C. and 60° C. for 4 hours, preferably in a dry environment. Drying the roots can in particular be made in a ventilated oven.

More advantageously, the plant extract comprising at least one compound according to the invention is prepared according to the process comprising the following steps of:
a) culturing plants synthesising at least one dicaffeoylquinic acid, and in particular *Ipomoea batatas* plants, under above-ground conditions,
b) solid/liquid extraction by root exudation of the plants from step a) in pure glycol or a glycol solution, in particular in dipropylene glycol or propane 1,3 diol, and
c) optionally, recovering the root extract obtained in step b).

Advantageously, the present invention thus relates to a process enabling an *Ipomoea batatas* extract to be prepared comprising at least one compound according to the invention and comprising:
culturing *Ipomoea batatas* under above-ground conditions,
solid/liquid extraction of *Ipomoea batatas* from the culturing step, by root exudation in glycol, in particular in dipropylene glycol or a dipropylene glycol solution,
possibly, solid/liquid extraction of *Ipomoea batatas* roots from the culturing step, which are freshly cut and possibly dried, by root exudation in glycol, in particular dipropylene glycol, and
possibly, recovering the extract(s) obtained during the extraction step.

According to another still more particular aspect of a process according to the invention:
the solid/liquid extraction by root exudation is implemented whereas said roots are still attached to the plant, in dipropylene glycol, or a dipropylene glycol solution, the pH of which is between 1.6 and 2.2 for 15 to 45 minutes, preferably for 30 minutes, said extraction is followed by cutting the roots, and then solid/liquid extraction by maceration of said cut roots, in dipropylene glycol, or a dipropylene glycol solution, the pH of which is between 1.6 and 2.2 for 48 hours, the extracts obtained are then recovered, mixed, and then concentrated, and the solvent is adjusted between 65% and 75% DPG and a pH between 2.9 and 3.1.

According to another advantageous aspect of a process according to the invention, culturing plants synthesising at least one dicaffeoylquinic acid, and in particular *Ipomoea batatas*, is followed by severing the roots, and possibly drying the roots, the solid/liquid extraction being implemented by maceration in a solvent chosen from: dipropylene glycol, propane 1,3 diol, propane 1,2 diol and butylene glycol.

According to a still more particular aspect, one object of the invention is a process comprising culturing *Ipomoea batatas* under above-ground conditions, severing and then drying the roots, and then a step of macerating the cut and dried roots in propane 1,3 diol the pH of which is between 0.8 and 1 for 2 to 8 days, followed by recovering the extract obtained. The solvent content is adjusted between 50% and 60%, by adding water. The extract pH is then adjusted between 4 and 4.4.

Another object of the invention is a plant extract likely to be obtained by a process according to the invention.

Applications

Cosmetic Compositions

To be referred to as a hormetin, a substance has to induce a defensive cellular response in particular by modifying the expression of some genes, called vitagenes (S. I. Rattan. *Ann. N. Y. Acad. Sci.* 1998, 854: 54-60), in which there are particularly the transcription factor Nrf-2 and genes induced or inhibited by this transcription factor and in particular genes coding for Heme-Oxygenase 1 (D. Gems, L. Partridge. *Cell Metabolism,* 2008, 7: 200-204), HSP70, NAD(P)H, glutamate cysteine ligase, glutathione S transferase pi, UDP-glucuronosyltransferase 1A6 and nitric oxide synthase. The inventors have found that the compounds according to the invention, or the plant extract comprising the compounds according to the invention, can be referred to as hormetic agents and can thus be used to mitigate or delay the appearance of the signs of skin intrinsic or extrinsic ageing.

The present invention thus relates to a cosmetic composition comprising as an active agent at least one compound according to the invention or an extract according to the invention and advantageously a cosmetically acceptable excipient.

The administration modes, dosages and optimum dosage forms of the cosmetic compositions according to the invention can be determined according to the criteria generally considered in establishing a cosmetic treatment suitable for a subject as for example skin type. Depending on the administration type desired, the cosmetic composition according to the invention can further comprise at least one cosmetically acceptable excipient. The cosmetic composition according to the present invention can further comprise at least one cosmetically acceptable adjuvant known to those skilled in the art, chosen from thickeners, preservatives, fragrances, colorants, chemical or mineral screens, moisturising agents, thermal waters, etc.

Advantageously, the cosmetic composition comprises at least one compound of the general formula (I) according to the invention or an extract according to the invention in an amount between 0.01 and 10%, in particular between 0.05 and 5%, more particularly between 0.1 and 2%, with respect to the total weight of the composition.

The present invention thus relates to a cosmetic composition comprising as an active agent at least one compound according to the invention or an extract according to the invention and advantageously a cosmetically acceptable excipient.

The cosmetic composition according to the invention can further comprise other cosmetically active agents, such as other anti-age agents; or moisturising agents; agents having a soothing, calming or relaxing activity; agents stimulating skin microcirculation; sebo-regulating agents for oily skin care; cleaning or purifying agents; anti-radical agents; anti-inflammatory agents; chemical or mineral sun screens, etc.

The cosmetically acceptable excipient can be chosen from polymers, silicon compounds, surfactants, rheology agents, humectants, penetration agents, oily compounds, waxes, emulsifiers, film-forming agents, fragrances, electrolytes, pH adjustors, antioxidant agents, preservatives, colorants, mother-of-pears, pigments and mixtures thereof.

The cosmetic composition according to the invention is advantageously intended to a topic application. It can in particular be in the form of a cream, milk, lotion, gel, serum, spray, foam, solution, ointment, emulsion, patch or mask.

The cosmetic composition according to the invention is for delaying or repairing the appearance of (intrinsic or extrinsic) ageing signs, and in particular of extrinsic ageing. Advantageously, it can be in particular for preventing or inhibiting epidermis destructuration, skin firmness or elasticity loss, the appearance of wrinkles, rednesses, or skin pigmentation spots. Actually, it enables a skin protective response to be induced against external aggressions (sun, light or UV exposure; stress; malnutrition), thus making it less sensitive to these aggressions. In addition, the cosmetic composition also enables the epidermis to be restructured, skin to be toned up, and/or wrinkle attenuation or resorption to be favoured.

Another object of the invention is a compound according to the invention, an extract according to the invention or a cosmetic composition according to the invention, for its use in preventing skin ageing, mitigating the effects of skin ageing, or delaying the appearance of said effects, in particular for reducing and/or delaying redness formation, wrinkle formation, loss of skin firmness, loss of skin elasticity and formation of skin pigmentation spots, in particular photo-induced pigmentation spots and/or senescence spots.

The invention also relates to the use as an active agent of a compound of the formula (I) according to the invention, or an extract according to the invention, in a cosmetic composition or for preparing a cosmetic composition, for preventing skin ageing, mitigating the effects of skin ageing, or delaying the appearance of said effects, in particular for reducing and/or delaying redness formation, wrinkle formation, loss of skin firmness, loss of skin elasticity and formation of skin pigmentation spots, in particular photo-induced pigmentation spots and/or senescence spots.

According to this aspect, a compound, an extract or a cosmetic composition according to the invention is used as a cosmetic agent for preventing skin ageing, mitigating skin ageing effects, or delaying the appearance of said effects.

The invention also relates to a compound of the formula (I) according to the invention, or an extract according to the invention, or a cosmetic composition according to the invention, for preventing skin ageing, mitigating the effects of skin ageing, or delaying the appearance of said effects, in particular for reducing and/or delaying redness formation, wrinkle formation, loss of skin firmness, loss of skin elasticity and formation of skin pigmentation spots, in particular photo-induced pigmentation spots and/or senescence spots.

The invention also relates to a skin cosmetic care method for preventing or delaying the appearance of (intrinsic or extrinsic) skin ageing effects, characterised in that it comprises applying on at least one body or face skin part a cosmetic composition according to the invention.

Advantageously, in the method according to the invention, the cosmetic composition is applied to a subject in need thereof, in particular in anticipation of or subsequently to a single or repeated exposure of the skin to an oxidative stress.

The following examples aim at illustrating the present invention.

EXAMPLES

Example 1: Preparation and Effect of *Ipomoea batatas* Root Extracts in DPG on Fibroblasts—"Anti-Age" DNA Chip Study In order to analyse the possibility that an extract according to the invention has an anti-age action, the expression variations of 92 genes involved in cellular and skin ageing induced by two *Ipomoea batatas* root extracts in fibroblasts have been measured by qRT-PCR, and compared with the variations induced by TGF-β1 (positive control), the latter having well-documented effects on some genes analysed.

1.1. Materials and Methods
Extract

Two *Ipomoea batatas* root extracts, having 3,5-DCQ concentrations of 1 g/L (extract STR-0003-P25-P0001) and 2 g/L (STR-0003-P12-P0002) respectively, have been prepared by root exudation in DPG of *Ipomoea batatas* plant cultivated above the ground. 3,5-DCQ is the main compound of both these extracts (12-15% mass of total dry solids). Both these extracts also comprise in a lesser proportion chlorogenic acid, DCQ DPG esters and other caffeic acid ester derivatives and their isomers. Therefore, this is a mixture of compounds of formula (I), wherein 3,5-DCQ is present with a vast majority.

Cell Culture

The study has been made on human dermis fibroblasts NHDFs (ATCC, CRL-2522, origin: foreskin) cultured as a single layer in DMEM medium (Invitrogen, 31885-049) containing 10% foetal calf serum (Invitrogen, 10270-106) and antibiotics (Penicillin/Streptomycin, Invitrogen, 15140-122). These cells have been maintained in a wet atmosphere at 37° C. containing 5% CO2.

Determining of the Analysis Concentrations of 2 Actives by a Cytotoxicity Study

In order to determine the optimum analysis concentration for the extract STR-0003-P25-P0001 and for the extract STR-0003-P12-P0002, a preliminary experiment has been made on fibroblasts NHDFs. This study consisted in evaluating the cell viability to MTS (3-(4,5-dimethythiazol-2-yl)-5-(3-carboxy-methoxyphenyl)-2-(4-sulfophenyl)-2H-tetrazolium) (Promega, G3581) after 24 hours of treatment by the products. The cells NHDFs have been seeded in 24-well plates, 24 h before the treatment with different concentrations of the products to be tested. At the end of this experiment, a non-cytotoxic concentration has been defined in order to conduct the measurement of the expression modifications of the target genes.

The following concentrations have been tested:
Extract STR-0003-P25-P0001: 0.5 µg/mL, 5 µg/mL, 25 µg/mL, 50 µg/mL, 75 µg/mL, 100 µg/mL, 150 µg/mL, 200 µg/mL, and 250 µg/mL;
Extract STR-0003-P12-P0002: 25 µg/mL, 50 µg/mL, 75 µg/mL, 100 µg/mL, 200 µg/mL.

Analysis of the Gene Expression Modifications
Extraction of Total RNA

The extraction of total RNAs has been made using the RNeasy Mini kit (Qiagen, 74106). After 24 h treatment, the cells have been rinsed with PBS and lysed in the lysis buffer (culture triplicates have been made for each condition). The extraction and purification of RNAs have been made according to the supplier's instructions. The total RNAs have then been preserved at −80° C.

Qualification of the RNAs by Spectrophotometry and Capillary Electrophoresis

The concentration of total RNAs has been determined by spectrophotometric measurement. The quality and integrity of the RNAs has then been checked by capillary electrophoresis (plate-form Agilent Bioanalyzer 2100).

Quantification of the RNAs by spectrophotometric measurement: an aliquot of each RNA has been diluted in RNAse-free water and its concentration has been determined using an Ultrospec 1100 Pro (Amersham) spectrophotometer.

Integrity of the RNAs by capillary electrophoresis on Agilent Bioanalyzer: the integrity of the total RNA has been evaluated by viewing electrophoresis peaks corresponding to the ribosomal RNAs. For the total RNAs of upper eukaryotes, the size of the ribosomal bands should be 1.9 kb for 18S-RNA and 4.7 kb for 28S-RNA. The intensity of the upper band should represent about twice the intensity of the lower band. Small diffuse bands representing RNAs with a lower molecular weight (RNAt and Ribosomal RNA 5S) can be present. When RNA is degraded, a spread of the bands of the ribosomal RNA as well as a noise for the RNAs with a higher molecular weight are observed.

Synthesis of the Complementary DNAs or DNAc

The reverse transcriptions (RT) have been made using the "High Capacity RNA-to-cDNA Kit" (Applied Biosystems, 4387406). For the synthesis of the DNAc, a mix has been prepared according to the supplier's instructions, with 2 µg total RNA, the ad hoc buffer provided in the kit and the reverse transcriptase enzyme. This reaction has been made as 37° C. for 1 hour, and then 5 minutes at 95° C. and finally the DNAc samples are placed on ice and stored at −20° C.

Preparation of the Taqman Microfluidic Chips, Performing the Quantitative PCR and Analysis of the Cts The reaction mixtures for PCR on TaqMan microfluidic chips, customised by Applied Biosystems, have been prepared by following the detailed instructions of the *Applied Biosystems Micro Fluidic Card Getting Started Guide*. In summary, 100 ng of DNAc have been added to a PCR specific mixture before being injected in the chip and dispersed by capillarity. After the chip has been centrifuged, this has been sealed before performing the quantitative PCR and analysis with the Applied Biosystems system7900HT, using the ABI PRISM® 7900 Sequence Detection System, SDS2.1 software. This program enabled cycle threshold Ct (cycle threshold of detection from which the DNA amount is such that the signal is significantly distinguished from the noise) to be measured. The analysis of the expression levels has been made using the Data Assist software from Applied Biosystems. The method used to calculate the gene expression modification is based on the Ct value.

1.2. Results

Determination of the Analysis Concentration of the Extracts by a Cytotoxicity Study A cytotoxicity study of the extract has been made on dermis fibroblasts. The solvent present in the products has been tested in parallel. For each tested concentration of the extract, the solvent STR-DPG70 has been tested alone at a concentration equivalent to that present in the extract.

0.08% SDS has been used as a cytotoxicity positive control in order to validate the experiment.

Figure 1:
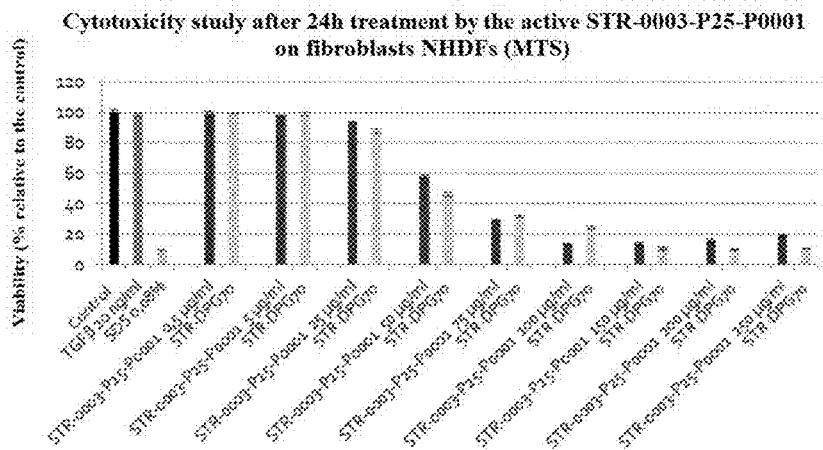
FIG. 1. Measurements of fibroblast NHDF viability after 24 h treatment with different concentrations of an *Ipomoea batatas* extract according to the invention (STR-0003-P25-P0001, in black), or of its solvent alone at the same concentration (STR-DPG70, in grey), or with TGF-$\beta_1$ (positive control of the expression variation of genes involved in the cellular or skin ageing). The viability percentages have been calculated with respect to the untreated negative control (Control) set to 100% and to the cytotoxicity positive control (0.08% SDS). The histograms represent the mean of 3 independent replicates and the error bar corresponds to the standard deviation from the mean.
Figure 2:
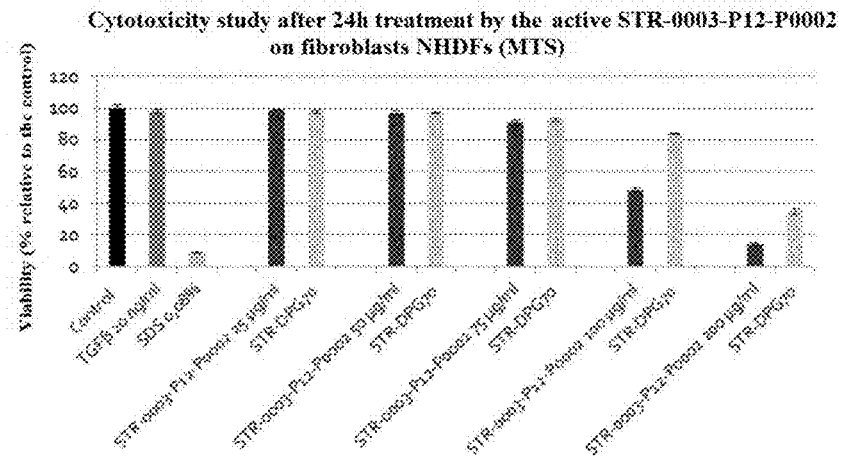
FIG. 2. Measurements of fibroblast NHDF viability after 24 h treatment with different concentrations of an *Ipomoea batatas* extract according to the invention (STR-0003-P12-P0002, in black), or of its solvent alone at the same concentration (STR-DPG70, in grey), or with TGF-$\beta_1$ (positive control of the expression variation of genes involved in the cellular or skin ageing). The viability percentages have been calculated with respect to the untreated control (CTL) set to 100%, and to the cytotoxicity positive control (0.08% SDS). The histograms represent the mean of 3 independent replicates and the error bar corresponds to the standard deviation from the mean.

The results are illustrated in FIGS. 1 and 2, and show that the extract STR-0003-P25-P0001 tested at 25, 5 and 0.5 µg/mL and the extract STR-0003-P12-P0002 tested at 25, 50 and 75 µg/mL induce no cytotoxicity. However, a morphological disturbance is observed (presence of some floating cells) when the cells are treated with 75 µg/mL active.

Based on these results, the following concentrations have been chosen for the following of the study: 25 µg/mL (Extract STR-0003-P25-P0001) and 50 µg/mL (Extract STR-0003-P12-P0002).

Qualification of the RNAs by Capillary Electrophoresis

The different RNA populations do show the presence of narrow peaks, corresponding to the ribosomal RNAs 18S and 28S, and a balanced ratio between both peaks. The absence of intermediate and spread peaks, characteristic of RNA degradation products is a mark of the integrity of the different populations (data not shown).

The quality and integrity of the extracted RNAs being demonstrated, hence, they can be used for continuing the protocol and be committed in the reactions for synthesising complementary DNAs.

Analysis of the Expression Modifications of Genes Induced by the Extracts STR-0003-P25-P0001 and STR-0003-P12-P0002 on Fibroblasts NHDFs The extracts STR-0003-P25-P0001 and STR-0003-P12-P0002 and the solvent (STR-DPG70) have been applied on fibroblasts, for 24 hours. At the end of the application, the total RNA populations have been extracted and analysed by qRT-PCR using a TaqMan chip targeting ageing and the extracellular matrix. As expected, TGF-β, a reference element (or "internal positive control") has some effect on a number of genes and hence validates the test system.

The results of the extract, expressed as RQ, relative expression, are found in table 3 and compared with the treatment by solvent STR-DPG70. The experiments have been made in culture triplicates. The values $0.01 < p < 0.05$ have been considered as significant, the values $0.001 < p < 0.01$ as highly significant and the values $p < 0.001$ as very highly significant.

TABLE 3

Comparative list of the genes modified at least significantly by the treatment by 25 µg/mL STR-0003-P25-P0001 extract or 50 µg/mL STR-0003-P12-P0002 extract.

| Name of the genes expressed | Symbol of the genes | STR-0003-P25-P0001 RQ | P-value | STR-0003-P12-P0002 RQ | P-value | General function |
|---|---|---|---|---|---|---|
| Heme Oxygenase (decycling) 1 | HMOX1 | 7,5492 | 0.0043 | 12,9967 | 0.0237 | Defence |
| Caveolin 1 | CAV-1 | 0.8456 | 0.0412 | 0.6953 | 0.0351 | signal transduction |
| Collagen, type III, alpha 1 | COL3A1 | 0.5397 | 6.00E−04 | 0.6831 | 0.0402 | cellular communication/focal adhesion/ECM-receptors interaction |
| Connective tissue growth factor | CTGF | 0.6982 | 0.0186 | 0.5252 | 0.0135 | Growth factors and cytokines |
| Fibulin 5 | FBLN5 | 0.6753 | 0.0252 | 0.7336 | 0.0265 | extracellular matrix |
| Fibroblast growth factor | FGF7 | 0.5991 | 0.0428 | 0.4304 | 0.0016 | Cellular growth |
| Glutathione peroxidase 1 | GPX1 | 0.3134 | 0.0091 | 0.3422 | 0.0032 | antioxidant enzymatic defence |
| Insulin-like growth factor 1 | IGF1 | 0.3232 | 4.00E−04 | 0.3089 | 0.0025 | Cellular growth |
| Insulin-like growth factor binding protein 3 | IGFBP3 | 0.5961 | 0.0274 | 0.3927 | 0.003 | cellular proliferation/apoptosis |
| Insulin-like growth factor binding protein 5 | IGFBP5 | 0.619 | 0.0138 | 0.5403 | 0.0072 | cellular proliferation/apoptosis |
| Retinoblastoma 1 | RB1 | 0.8212 | 0.0197 | 0.6759 | 0.0232 | Cellular cycle |
| Thymidine kinase 1 | TK1 | 1.1985 | 0.0023 | 0.4939 | 0.0034 | pyrimidine metabolism |
| Heat shock 70 KDa protein 1A | HSPA1A | 1.8348 | 0.0281 | | | defence |
| NAD(P)H dehydrogenase, quinone 1 | NQO1 | 1.7295 | 0.0265 | | | antioxidant enzymatic defence |
| Activator protein 1 | JUN | 1.4691 | 0.0119 | | | Transcription factor activity |
| Proliferating cell nuclear antigen | PCNA | 0.8358 | 0.0189 | | | DNA repair |
| Ataxia telangiectasia mutated | ATM | 0.8223 | 0 | | | DNA repair/synthesis |
| Calnexin | CANX | 0.7974 | 0.0404 | | | Protein folding and assembly |
| Polymerase (RNA)II (DNA directed) polypeptide A | POLR2A | 0.7747 | 0.0095 | | | Housekeeping gene |
| Fibrillin 1 | FBN1 | 0.771 | 0.0447 | | | extracellular matrix |
| BCL2-associated X protein | BAX | 0.7407 | 0.0199 | | | apoptosis |

TABLE 3-continued

Comparative list of the genes modified at least significantly by the treatment by 25 µg/mL STR-0003-P25-P0001 extract or 50 µg/mL STR-0003-P12-P0002 extract.

| Name of the genes expressed | Symbol of the genes | STR-0003-P25-P0001 RQ | P-value | STR-0003-P12-P0002 RQ | P-value | General function |
|---|---|---|---|---|---|---|
| Forkhead box 3 | FOXO3 | 0.7405 | 0.026 | | | Transcription factor |
| 8-oxoguanine DNA glycosylase | OGG1 | 0.6915 | 0.0139 | | | DNA repair |
| Matrix metallopeptidase 2 | MMP2 | 0.6699 | 0.0305 | | | extracellular matrix |
| Syndecan 3 | SDC3 | 0.6693 | 0.0049 | | | Cellular form, cellular signalling |
| Sirtuin 2 | SIRT2 | 0.6607 | 0.0306 | | | Gene silencing |
| Secreted protein, acidic, cysteine-rich (osteonectin) | SPARC | 0.6297 | 0.0156 | | | extracellular matrix |
| Collagen, type I, alpha 2 | COL1A2 | 0.6128 | 0.0097 | | | cellular communication/focal adhesion/ECM-receptors interaction |
| Elastin | ELN | 0.3824 | 0.05 | | | extracellular matrix |
| Growth arrest and DNA-damage-inducible | GADD45A | | | 1.2345 | 0.0343 | DNA repair |
| Lysyl oxidase-like 1 | LOXL1 | | | 0.7837 | 0.0435 | extracellular matrix |
| Peroxiredoxin 5 | PRDX5 | | | 0.7794 | 0.0475 | defence |
| Transforming growth factor, beta 1 | TGFB1 | | | 0.6821 | 0.0281 | Cellular proliferation |
| Heat shock 27 KDa protein 1A | HSPB1 | | | 0.5339 | 0.0023 | defence |
| V-Fos FBJ murine osteosarcoma viral oncogene | FOS | | | 0.4793 | 0.0088 | cellular cycle |
| Matrix metallopeptidase 3 | MMP3 | | | 0.4585 | 0.0395 | extracellular matrix |
| Transgelin | TAGLN | | | 0.364 | 4.00E−04 | cellular structure |

Generally, the analysis of table 3 shows that:
a few genes are overexpressed in response to the extracts STR-0003-P25-P0001 and STR-0003-P12-P0002. However, the HMOX gene is widely overexpressed by a factor 7.5× and 13× in response to both extracts STR-0003-P25-P0001 and STR-0003-P12-P0002 respectively. This overexpression can be referred to as quite remarkable. To a lesser extent, HSPA1A and NQO1 are also overexpressed by a factor 1.8× and a factor 1.7× respectively in response to the extract STR-0003-P25-P0001.
Further genes are repressed.
The overexpression of GPX1 and IGF1 genes (more than 3×, RQ<0.33) has been highlighted for both extracts STR-0003-P25-P0001 and STR-0003-P12-P0002. The overexpression of more than 2× (RQ<0.5) of elastin in response to the extract STR-0003-P25-P0001, and of transgelin by the extract STR-0003-P12-P0002 can also be noted.

1.3. Discussion

Overexpression of the "Vitagenes"

HMOX and HSPA1A genes belong to the vitagene family, further comprising the transcription factor Nrf-2 (HSP32), the chaperone protein HSP60 and the thioredoxin system genes. These genes are most often overexpressed in response to a stress, and play a crucial role in protecting and maintaining cellular homeostasis.

The protein HSP70 (coded by the gene HSPA1A) is a chaperone molecule (heat shock protein 70) which inhibits aggregation of denaturated proteins, promotes their renaturation (refolding) and controls mediators essential for the apoptic machinery.

The overexpression of HO-1 or HSP70 vitagenes as a result of cellular stresses, in particular of the radical type, is associated with the hormesis concept, which relies on the fact that a molecule or a treatment generating a low intensity stress, without significant cellular damage, enables a protective and antioxidant response to be induced in order to ensure homeostasis of the cell (to pro-oxidant molecules, a thermal stress, hormones, energy restriction, etc.), thus preparing and protecting the cell against subsequent stresses with a higher intensity.

Overexpression of the NQO1 Gene

The NQO1 gene codes for the NAD(P)H dehydrogenase (quinone), having a 2-electron reductase cytoplasmic activity being the mark of a detoxifying action. NQO1 is overexpressed in response to pro-oxidant agents, heavy metals, UV or even ionising radiations. NQO1 stabilises the protein p53 controlling various repair enzymes and apoptosis mediators. The NQO1 enzyme promotes hydroquinone formation from quinones by reduction, preventing radical species from being produced. NQO1 is under the control of the transcription factor Nrf-2 controlling the response pathway to an oxidative stress (Nguyen et al, Biol. Chem., 284 (20), 13291-13295, 2009).

It has been demonstrated that the protein NQO1 is associated with the protein HSP70 to enhance its stability and activity (Anwar et al., J. Biol. Chem., 277, 14060-14067, 2002). The overexpression of NQO1 induced by STR-0003-P25-P0001 and STR-0003-P12-P0002 is thereby in favour of a protective activity towards a cellular stress.

Underexpression of GPX1, IGF1 Genes, Elastin and TAGLN

The GPX1 gene codes for glutathione peroxidase 1, involved in H2O2 detoxification endogenously produced by mitochondrial breathing and ATP synthesis (oxidative phosphorylation). In this case, the gene repression is not correlated with an antioxidant activity of the products.

The IGF1 gene codes for a growth factor, called insulin growth factor 1. The decrease in circulating IGF1 and the inactivation of the IGF1 gene have been associated with an increase in the longevity of model organisms such as *C. elegans* nematode or mice.

The ELN gene codes for tropoelastin, which is one of the major components of the elastic fibres with fibrillin. The crosslinking of tropoelastin, catalysed by lysyl oxidase, forms elastin, the decrease with age of which results in wrinkle formation.

Finally, the TAGLN gene codes for transgelin, also called SM22, the overexpression of which is recognised as a robust biomarker of the senescent fibroblasts.

1.4. Conclusion

The induction of the HMOX, HSP70 and NQO1 genes suggests that an extract according to the invention or the molecule 3,5-DCQ, which is high by a wide majority in extracts STR-0003-P25-P0001 and STR-0003-P12-P0002, could exert a protective effect towards radical stresses which are endogenous and related to the chronological ageing, or exogenous as induced by UVAs or various pollutant agents, by a mechanism based on the hormesis principle.

Example 2: Induction Kinetics of Proteins Coded by the HMOX, HSP70 and NQO1 Genes as a Result of the Application of *Ipomoea batatas* Root Extracts in DPG and Confirmation of the Protective Effect of the Exposure of Fibroblasts to *Ipomoea batatas* Root Extracts in DPG Towards Oxidative Stresses Subsequent to UVs It has been shown in Example 2 that contacting fibroblasts with two *Ipomoea batatas* root extracts comprising as a main compound 3,5-DCQ, induces an overexpression of proteins involved in the hormesis process at the RNAm level. In order to confirm the induction of an overexpression of these proteins by these extracts at the protein level, analyses have been made by Western Blot.

2.1. Materials and Methods
Extract

Two *Ipomoea batatas* root extracts, having 3,5-DCQ concentrations of 1 g/L (extract STR-0003-P33-P0004) and 2 g/L (STR-0003-P33-P0003) respectively have been prepared as described in example 1. 3,5-DCQ is the main compound of both these extracts (12-15 mass % of the total dry solids). Both these extracts also comprise in a lesser proportion chlorogenic acid and other caffeic acid ester derivatives and their isomers. Thus, this is a mixture of compounds of the formula (I), wherein 3,5-DCQ is present with a vast majority. As in example 1, the extract STR-0003-P33-P0004 has been used at a 25 µg/mL concentration, whereas the extract STR-0003-P33-P0003 has been used at a 50 µg/mL concentration.

Cell Culture

The study has been made on human dermis fibroblasts NHDFs (ATCC, CRL-2522, origin: foreskin) cultured in single layer in DMEM medium (Invitrogen, 31885-049) containing 10% foetal calf serum (Invitrogen, 10270-106) and antibiotics (Penicillin/Streptomycin, Invitrogen, 15140-122). These cells have been maintained in a wet atmosphere at 37° C. containing 5% $CO_2$.

Determination by Western Blot of the Induction Kinetics of HO-1/HSP32 at the Protein Level The cultivated fibroblasts have been put in presence of the actives during 6, 24, 48 or 72h. The concentrations chosen for both actives (50 µg/mL for the extract STR-0003-P33-P0003 and 25 µg/mL for STR-0003-P33-P0004) have been determined following the study of the analysis concentrations by a cytotoxicity study described in example 2.

The positive control of the experiment inducing the expression of the protein HO-1 is celastrol (Sigma, C0869) used at 250 nM.

Protein Extraction

The proteins have been directly extracted after applying the actives, after 6, 24, 48 or 72 hours of contact, using a T-PER (Tissue Protein Extraction Reagent, Pierce, ref 78510) solution associated with a phosphatase inhibitor (PhosSTOP, Roche, ref 04 906 837 001) and a protease inhibitor (Complete Protease inhibitor cocktail, Roche, ref 04 693 116 001). The lysates have then been vortexed and cold sonicated before being centrifuged in order to remove the cellular debris. The supernatants obtained have been freezed at −80° C.

Protein Assay

The protein content of the cellular lysates has been quantified by a colorimetric method, using the 660 nm Protein Assay Reagent (Pierce, ref 22662). The optical densities obtained for the samples and reference solutions (Pre-diluted Protein Assay standards: BSA Set, ref 23208, Thermo Scientific) have been used in order to calculate the protein concentration of each sample.

Western Blot

The samples have been loaded on 10% polyacrylamide gels (Invitrogen, ref NP0301BOX) with 10 µg proteins per sample. The migration has been made for 1 hour at 200 Volt. The transfer step onto a PVDF membrane (Polyvinylidene fluoride membrane, Pa011 Corporation, ref P/N66543) has been made on ice, for 1 hour at 100 Volt. The membranes have been saturated in a 2% milk solution (ECL detection kit, Amersham, RPN2135). Then, the membranes have been incubated overnight, at 4° C., with the protein specific antibody HO-1/HSP32 (BD, ref 610712). After rinsing, the membranes have been put in presence of the secondary antibody, coupled with the peroxidase (HRP). The band viewing has been made with the kit containing chemiluminescent substrates (ECL detection kit, Amersham, RPN2135) and autoradiography films (hyperfilm ECL, Amersham, 28-9068-36). Tubulin-α has been used as a reference protein in order to normalise the values. The band intensity quantification has been made using the ImageJ software.

Highlighting the Protective Effect of the Actives Towards a Pro-oxidant Radical Stress: Validation of the Hypothesis of a Hormetic Effect of the Actives Confirmation of the Induction of a Radical Stress by the Actives In order to validate the hypothesis of a hormetic effect, it has been checked beforehand that the treatment by the actives alone induced a radical stress. The test used is based on the use of the fluorescent probe H2DCFDA (2'-7'dichlorodihydrofluorescein diacetate, Fischer Scientific, #D399). The probe diffusion into the cell enables its acetate group to be cleaved by intracellular esterases. Since then, the probe can be oxidised by free radicals (reactive oxygen species (ROS)) into DCF (2'-7'-dichlorofluorescein), that is a fluorescent compound. The production of free radicals can thus be quantised by the level of fluorescence emitted by the probe oxidised. In practice, the cells have been treated for 4 or 6 hours by the actives and at the end of these treatments, the cells have been rinsed and then put in presence of the H2DCFDA probe at 5 µM for 1 hour at 37° C., 5% CO2 in order to allow it to diffuse intra-cellularly. After rinsing, the fluorescence emitted has been quantised (excitation: 485 nm; emission: 520 nm).

In order to provide a result representative of the cellular population of each condition, a cellular viability test (MTS) has been made immediately after quantising the fluorescence emitted. The fluorescence values have thus been normalised with respect to the cellular viabilities.

Highlighting the Protective Effect of the Actives Towards a UVA Non-cytotoxic Radical Stress The protective effect of the test elements towards a UVA non-cytotoxic stress (10 J/cm$^2$) on fibroblasts has also been evaluated by a test based on the use of the fluorescent probe H2DCFDA. The data obtained have been normalised with respect to the cellular viability (MTS test).

In practice, the cells have been treated for different times (4 h and 6 h) with the actives. The cells have then been rinsed and reput in a fresh medium for 16 further hours. At the end of these 16 recovery hours, the cells have been rinsed with PBS and then put in presence of the probe H2DCFDA at 5 µM for 1 hour at 37° C., 5% CO2 in order to allow it to diffuse intra-cellularly. After rinsing, the cells have been subjected to a UVA stress at 10 J/cm$^2$. A non-exposed condition has been made in parallel. The quantisation of the fluorescence emitted (excitation: 485 nm; emission: 520 nm) has been immediately performed after the end of the UVA stress. As previously, a MTS viability test has been made in order to normalise the fluorescence with respect to the cellular viability.

2.2, Result

Figure 3:
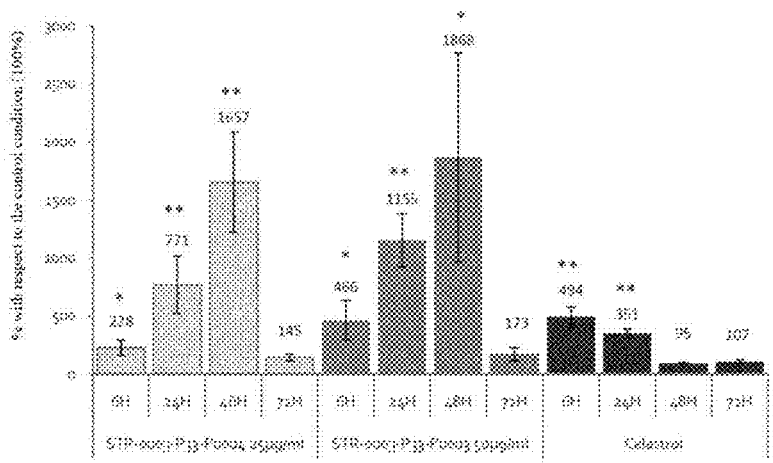
FIG. 3. Quantification of the protein HO-1/$HSP_{32}$ in fibroblasts treated with the extracts according to the invention STR-0003-P25-P0003 and STR-0003-P12-P0004 for 6 h, 24 h, 48 h, and 72h. The positive control of the experiment inducing the expression of the protein HO-1 is celastrol used at 250 nM. The graph represents the mean of the measurements made on the lysates from 3 independent cultures per condition, as well as the standard deviation. The statistical analysis conducted with a student t-test enabling the individual effect of each of the treatments to be compared with respect to the control condition (untreated control for both actives and 0.05% DMSO control for celastrol) set to 100% (*: $0.01 < p < 0.05$; **: $0.001 < p < 0.01$). The values $0.01 < p < 0.05$ have been considered as significant and the values $0.001 < p < 0.01$ as highly significant.

Determination by Western Blot of the Induction Kinetics of HO1-1/HSP32 at the Protein Level FIG. 3 shows the expression analysis of the protein HSP32/HO-1 by fibroblasts treated by negative control media (CTL DMSO et CTL), a positive control product (Celastrol) and by the extracts STR-0003-P33-P0004 (25 µg/mL) and STR-0003-P33-P0003 (50 µg/mL), after 6 h, 24 h, 48h or 72 h incubation respectively.

They confirm that the extracts STR-0003-P33-P0004 and STR-0003-P33-P0003 induce an overexpression of the protein HSP32/HO-1 in fibroblasts, thus generating a protective response in these cells, which response is likely to protect them against subsequent stresses.

Highlighting the Protective Effect of the Actives Towards a Pro-oxidant Radical Stress: Validation of the Hypothesis of a Hormetic Type Mechanism.

Confirmation of the Induction of a Radical Stress by the Extracts Studied after 4 and 6 Hours of Contact Firstly, in order to demonstrate that the extracts studied protect cells from a radical stress, by behaving as a hormetin, the production of reactive oxygen species (ROS) has to be measured at the end of a 4 and 6 hours of contact with these extracts and demonstrate that they generate a non-cytotoxic stress, in particular a radical stress.

Figure 4:
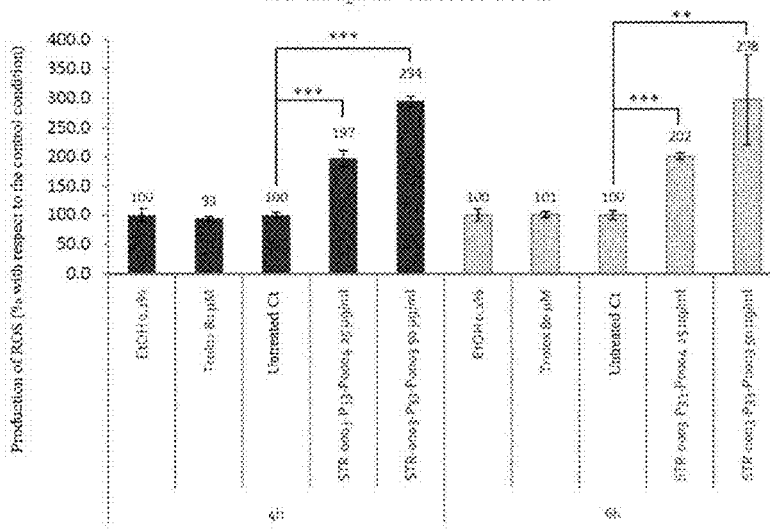
FIG. 4. Quantification of the production of reactive oxygen species (ROS) after the treatment of the fibroblasts NHDFs by two *Ipomoea batatas* extracts according to the invention STR-0003-P33-P0003 and STR-0003-P33-P0004 for 4 or 6 hours. The data have been normalised with respect to the cell viability evaluated by a MTS test after the ROS assay. The graph represents the mean of the values obtained from 3 independent cultures per condition, as well as the standard deviation. The statistical analysis conducted is a student t-test enabling the individual effect of each of the treatments to be compared with the control condition (untreated control for both actives and 0.1% EtOH for Trolox) set to 100%. (*: $0.01 < p < 0.05$; : $0.001 < p < 0.01$; *: $p < 0.001$). The values $p < 0.05$ have been considered as significant, the values $0.001 < p < 0.01$ as highly significant and the values $p < 0.001$ as very highly significant.

This experiment has demonstrated that the treatment of the fibroblasts alone by the actives (for 4 or 6 hours) actually induce a radical type stress. In parallel, the treatment by an antioxidant neutralising free radicals by a conventional oxidation-reduction reaction, that is Trolox, a soluble vitamin E analogue (Sigma 238813), induces no radical stress since it does not act according to a hormetic mechanism. The results obtained are summarised in FIG. 4. The fluorescence values have been normalised with respect to the cellular viability evaluated by a MTS test. The results are expressed in percentages with respect to the control condition (0.1% EtOH for the Trolox treatment and untreated control for the treatment by the actives).

Highlighting the Protective Effect of the Actives Towards a UVA Non-cytotoxic Radical Stress.

Secondly, in order to demonstrate a protective effect related to the application of the extracts for 4 and 6 hours, to a stress applied at the end of a recovery period of 16 hours.

Figure 5:
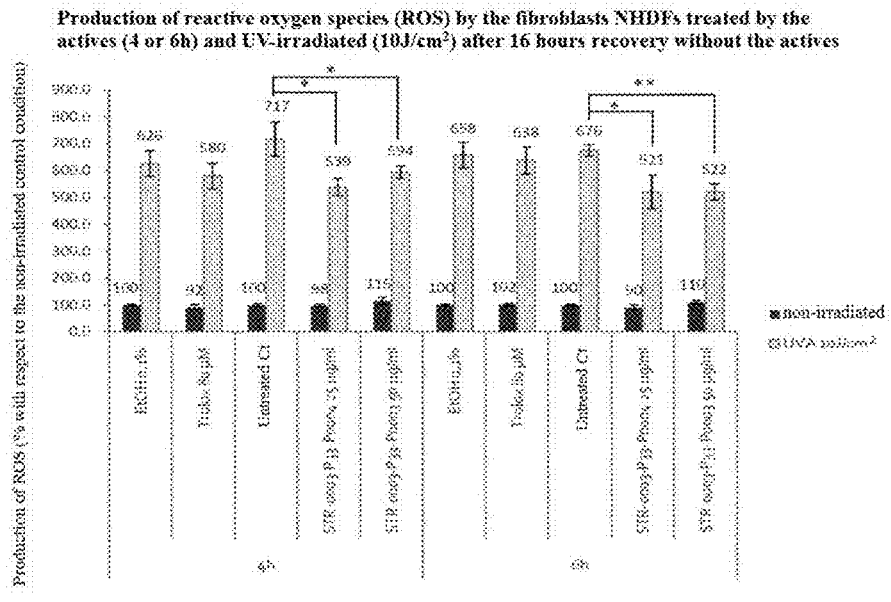
FIG. 5. Quantification of the production of reactive oxygen species (ROS) by the fibroblasts NHDFs after a UVA stress (10 J/cm$^2$). The cells have been pre-treated for 4 or 6 h by the extracts STR-0003-P33-P0003 and STR-0003-P33-P0004 and then have been recovered for 16 hours in a fresh medium. At the end of these 16 hours, the UVA stress has been made and the ROS production has been quantised by fluorescence measurement. The fluorescence data have been normalised with respect to the cell viability evaluated by MTS after the UVA stress and ROS assay. The graph represents the mean of the values obtained from 3 independent cultures per condition, as well as the standard deviation. The statistical analysis conducted is a student t-test enabling the individual effect of each of the treatments to be compared with respect to the control condition (untreated control for both actives and 0.1% EtOH for Trolox) set to 100%. (*.

The results illustrated in FIG. 5 show that an incubation with the actives for short times (4 or 6h) followed by 16 hours of recovery protects cells against the formation of free radicals induced by a UVA non-cytotoxic stress. This kinetics has been developed beforehand and has been duly optimised. As previously, the fluorescence data have been normalised with respect to the cell viability, evaluated by a MTS test after the UVA stress. The results confirm the hypothesis of a protective effect induced by the actives, consisting in mitigating the free radical production after a UVA exposure.

2.3. Conclusion

At the end of these studies, the experiments made demonstrating a strong induction of the protein HO-1 as well as a protective effect of a contact of the cells with the extracts, towards the effects of a UVA exposure, which is the main cause of skin photo-ageing, enable the extracts STR-0003-P33-P00003 and STR-0003-P33-P00004 of hormetins to be qualified. The use of these extracts is thus suitable in skin care products and could be a new way to fight against skin ageing.

Example 3: Determination of the Fractions and Compounds Contained in the *Ipomoea batatas* Root Extracts According to the Invention Having a Hormetic Effect on Fibroblasts: "Anti-age" DNA Chip Study It has been demonstrated in examples 1 and 2 that an *Ipomoea batatas* extract according to the invention can be referred to as a hormetin.

In order to determine which fraction of the extract according to the invention is responsible for this effect, the expression variations of seven target markers (involved in cellular and skin ageing induced by four fractions of an *Ipomoea batatas* root extract, and by the extract itself, in fibroblasts have been measured by qRT-PCR. A condition corresponding to fibroblasts NHDFs irradiated with UVA (10 J/cm$^2$) has been analysed in parallel as a positive control for the test.

The seven markers studied (HOMX1, NQO1, HSPA1A, GCLM, GSTP1, UGT1A6 and NOS2) are genes the expression of which is known to be regulated by the transcription factor Nrf-2, playing a major role in the antioxidant defence.

3.1. Materials and Methods

Extract

An *Ipomoea batatas* root extract (PAT0014), having a 3,5-DCQ concentration of 1.1 g/L, has been prepared in DPG as described in example 1. 3,5-DCQ is the main compound of this extract (11% mass of the total dry solids). This extract also comprises at least one compound according to the invention and to a lesser extent, chlorogenic acid and other caffeic acid ester derivatives and their isomers.

Fractions

The main compounds of the *Ipomoea batatas* root extract studied are mentioned in the following table 4:

TABLE 4

Main compounds of the fractions studied

| Fractions | Main compounds |
|---|---|
| STL964 | 3,4-DCQ (Isochlorogenic acid B) |
| STL965 | 3,5-DCQ (Isochlorogenic acid A) |
| STL967 | 4,5-DCQ (Isochlorogenic acid C) |
| STL1654 | 3,5-DCQ DPG esters |

The four fractions also comprise to a lesser proportion chlorogenic acid and other caffeic acid ester derivatives and their isomers. Fraction STL1654 corresponds to a plant extract mainly comprising at least one compound of the general formula (I) according to the invention and can further comprise DCQs to a lesser proportion.

The fractions STL964, STL965, STL967 have been isolated from the raw extract by purification on a preparatory column (C18). Each fraction has been characterised by NMR (1H and 13C) and mass spectrometry (LC/MS). Fraction STL1654 has been obtained by hemisynthesis from the fraction STL965, according to the process described below:

Reagents

| Reagent | CAS | Providers | Molecular formula | MW | Sample mass (mg) |
|---|---|---|---|---|---|
| 3,5-DCQ—Isochlorogenic acid A—(=STL965) | 2450-53-5 | Synthelor | $C_{25}H_{24}O_{12}$ | 516.45 | 100 |
| Dipropylene glycol (DPG)/Mixture of isomers | 25265-71-8 | | $C_6H_{14}O_3$ | 134.17 | 1039 |
| Amberlite IR-120H (Plus) | 78922-04-0 | Aldrich | | | 10 |

Reaction

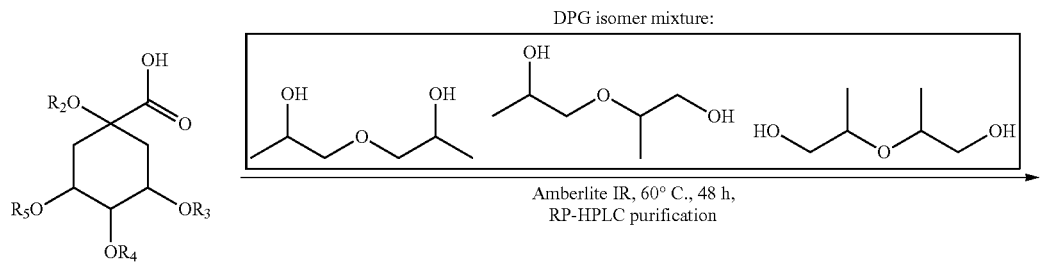

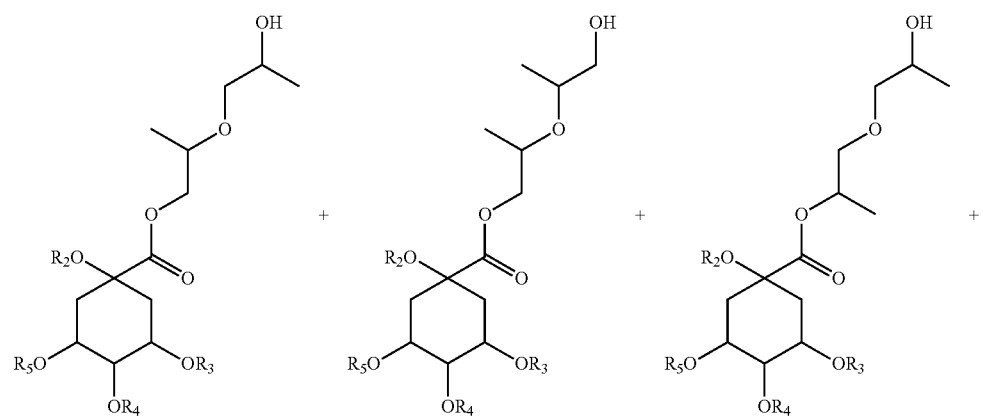

-continued

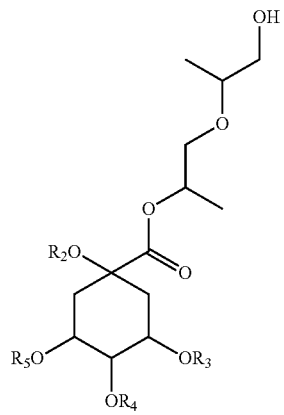

Preparation

The fraction STL965 (100 mg, 0.194 mmol) is dissolved in dipropylene glycol (DPG) corresponding to a mixture of isomers of the formulae (VIa), (VIb) and (VIIc) (1019 µl, 7.75 mmol). Amberlite IR-120H (Plus) (10 mg, 0.194 mmol) is added and the reaction mixture is heated at 60° C. for 72 ours under argon and low stirring in a hermetically sealed tube.

The reaction medium is diluted in 1M HCl, filtered and then extracted 3 times in ethyl acetate. The combined organic phases are successively washed with 1M HCl (1×), brine, dried on $MgSO_4$, filtered and evaporated under vacuum. The residue obtained is dissolved in 500 µL of a 1/1 acetonitrile/water solution.

The raw solution obtained is then purified by RP-HPLC on a C18 column (Luna, 250×21.2 mm, 5 µm) at a 20 mL/min flow rate and by UV detection at 254 nm. The pure fractions are mixed together and lyophilized to obtain the DCQ DPG esters.

Cell culture

The study has been made on human dermis fibroblasts NHDFs (ATCC, CRL-2522, origin: foreskin) at about 40% of their proliferative potential in vitro. These cells have been cultivated in single layer in DMEM medium (Invitrogen, 31885-049) containing 10% foetal calf serum (Invitrogen, 10270-106) and antibiotics (penicillin/streptomycin, Invitrogen, 15140-122). These cells have been maintained in a wet atmosphere at 37° C. containing 5% $CO2$.

Determination of the Analysis Concentration of the 4 Fractions and of the Extract Itself by a Cytotoxicity Study In order to determine the optimum analysis concentration for the fractions, a preliminary experiment has been made on human dermis fibroblasts NHDFs having performed 30.3 population doublings. This study consisted in evaluating cell viability to MTS (3-(4,5-dimethythiazol-2-yl)-5-(3-carboxy-methoxyphenyl)-2-(4-sulphophenyl)-2H-tetrazolium) (Promega, G3581) after 24 h treatment for the 4 fractions, at 5 concentrations (100 µM, 50 µM, 25 µM, 12.5 µM, and 6.25 µM) and in culture triplicates (n=3). The fractions and extract have been prepared in DMSO and DPG70 respectively, the effect of these 2 vehicles has also been tested.

0.08% SDS (sodium dodecyl sulphate) has been used as a cytotoxicity positive control in order to validate the experiment.

Analysis of the Gene Expression Modifications

Extraction of Total RNA

The extraction of total RNAs has been made using the RNeasy kit (Qiagen, 74106), after 24 h treatment with the fractions or 6 h after UVA irradiation. The cells have been rinsed with PBS and lysed in ad hoc buffer (culture triplicates have been made for each condition). The extraction and purification of the RNAs have been made according to the supplier's instructions. The total RNAs have been preserved at −80° C. afterwards.

Qualification of the RNAs by Spectrophotometry and Capillary Electrophoresis

The concentration of the total RNAs has been determined by spectrophotometric measurement. The quality and integrity of the RNAs has then been checked by capillary electrophoresis (plate-form Agilent Bioanalyzer 2100):

Quantification of the RNAs by spectrophotometric measurement: an aliquot of each RNA has been diluted in RNAse-free water and its concentration has been determined using an Ultrospec 1100 Pro spectrophotometer (Amersham).

Integrity of the RNAs by capillary electrophoresis on Agilent Bioanalyzer: the integrity of the total RNA has been evaluated by viewing the electrophoresis peaks corresponding to the ribosomal RNAs. For the total RNAs of upper eukaryotes, the size of the ribosomal bands should be 1.9 kb for 18S-RNA and for 4.7 kb for 28S-RNA. The intensity of the upper band should have an intensity higher than that of the lower band. Small diffuse bands representing RNAs having a lower molecular weight (RNAt and ribosomal RNA 5S) can be present. When the RNA is degraded, a spread of the ribosomal RNA bands as well as a noise of the RNA with a higher molecular weight are observed.

Real Time qPCR Using TaqMan Type Probes

The real time qPCR method has been used to quantise the expression of target markers in the different populations of RNAs. The specific TaqMan probes have been synthesised by the company Applied Biosystems.

The target sequences of the genes of interest have been amplified by PCR by using the "TaqMan Gene Expression Assays" (Applied Biosystems). These kits specific to the genes of interest comprise a TaqMan probe and 2 specific primers, which have been pre-mixed at an 18 µM concentration for each primer and 5 µM for the probe. This mixture is 20 times concentrated. The TaqMan probes have been grafted with a fluorophore (FAM) at the 5' end of the sequence with a 3' fluorescence quencher.

The PCR have been made using the Fast Real-Time PCR system 7900HT (Applied Biosystems). The reactions have been made in a 20 µL volume. The reaction mixture contains 10 µL TaqMan Fast Universal Master Mix (Applied Biosystems), 1 μL TaqMan Gene Expression Assay and 5 μL RNAse-free water. In each well of a 96-well microplate, 16 μL of the mixture and 4 μL of DNAc (4 ng) have been added. For the purpose of normalisation, reaction mixtures with probes and primers corresponding to glyceraldehyde-3-phosphate dehydrogenase (GAPDH) have also been prepared with the same DNAc samples. A control without DNAc acts as an amplification negative control. The thermal cycles have been programmed with an incubation step at 50° C. for 2 minutes, followed by a first denaturation step at 95° C. for 10 minutes. The PCR amplification protocol continued with 40 cycles of 15 seconds at 95° C. and 1 minute at 60° C.

The relative expression levels have been quantised according to the relative expression calculation method with respect to a housekeeping gene (2-Ct), derived from the calculation of the ΔΔCts (Pfaffl, 2001 & Livak and Schmittgen, 2001).

3.2. Results

Determination of the Analysis Concentration of the 4 Fractions by a Cytotoxicity Study In order to determine the optimum study concentration of the 4 fractions, a cytotoxicity study has been made on human dermis fibroblasts NHDFs, based on 5 concentrations after 24 h contact (n=3). The experimental parameters were identical to those used in the following for the study of the effects on the gene expression in terms of culture passages of the cells, confluence and contact time. The effect of the 2 vehicles (DPG70 and DMSO) has been tested in parallel.

The results have been compared to the untreated control and 0.08% SDS has been used as a cytotoxicity positive control in order to validate the experiment. The cytotoxicity threshold has been arbitrarily set to 80% viability.

The results are exhibited in FIG. 6 and show that the fractions STL964, STL965, STL967 and STL1654 as well as the 1% DMSO vehicle have no cytotoxicity.

Based on these results and in order to compare the effects of the fractions, the optimum working concentration for each of them has been set to 50 μM.

Qualification of the RNAs by Capillary Electrophoresis

The quality and integrity of the extracted RNAs have been evaluated by capillary electrophoresis. The profiles obtained are a mark of the integrity of the different populations of RNA. Then, the samples could be used in synthesis reactions of the complementary DNAs.

Analysis of the Expression Modifications of Genes Induced by the Different Plant Extract Fractions Among the five candidates studied, no expression has been detected for UGT1A6 and NOS2, regardless of the condition studied. The corresponding genes thus do not seem to be expressed by the fibroblasts NHDFs. The expression profiles of the RNAm targeting HMOX1, HSPA1A, NQO1, GCLM and GSTP1 after treating the fibroblasts NHDFs with the fractions and extract are illustrated in FIGS. 7 to 11. The expression levels are expressed as percentages with respect to the respective controls.

The UVA irradiated control condition (10 J/cm$^2$) has been compared to the control condition PBS, the conditions treated by the fractions STL964, STL965, STL967 and STL1654 have been compared to the 0.5% DMSO control condition (vehicles of these fractions) and the conditions treated by the *Ipomoea batatas* extract PAT0014 have been compared to the 2.5% DPG70 control condition (vehicle of the extract).

The statistical analysis performed is based on a student t-test individually comparing each treatment with its control (*: $p<0.05$; : $0.001<p<0.01$ and *: $p<0.001$). The values $p<0.05$ have been considered as significant, the values $0.001<p<0.01$ as highly significant and the values $p<0.001$ as very highly significant.

FIGS. 9 and 10 show that, among the fractions tested during the present study, the fraction STL1654 containing the DCQ DPG esters enables the expression of the NQO1 gene coding for the NAD(P)H dehydrogenase quinone 1 (FIG. 9) and the GCLM gene coding for the glutamate cysteine ligase (FIG. 10) to be very significantly induced.

The fraction STL1654 containing the DCQ DPG esters also tends to induce an overexpression of the HMOX-1 gene coding for heme oxygenase-1 (HO-1) (FIG. 7), the HSPA1A gene coding for protein HSP70 (FIG. 8), and the gene GSTP1 coding for the glutathione S transferase pi (FIG. 11).

Finally, FIGS. 2 to 6 show that the extract PAT0014 enables an overexpression of the HMOX-1 gene (FIG. 7) and the GCLM gene (FIG. 10) to be very significantly induced, but has no influence on the expression of the HSPA1A (FIG. 8), NQO1 (FIG. 9) and GSTP1 (FIG. 11) genes.

Unlike the fraction STL1654, the fractions STL964, STL965 and STL967 containing DCQs do not induce an overexpression of genes of interest (FIGS. 7 to 11).

3.3. Conclusions

The induction of the Nrf-2 stress response gene demonstrate that an extract comprising at least one compound of the general formula (I) according to the invention, exerts a protective effect towards radical stresses which are endogenous related to chronological ageing, or exogenous as induced by UVAs or various pollutant agents, and by a mechanism based on the hormesis principle.

The study of the different fractions of an *Ipomoea batatas* extract also makes it possible to demonstrate that the DCQ DPG esters originate this protective effect towards the oxidative stress, unlike the DCQs.

Example 4: Preparation and Effect of *Ipomoea batatas* Root Extracts in DPG or Propane 1,3 Diol, on Human Fibroblasts and in Melanised and Reconstituted Human Epidermis—"GeneChip Human Gene" DNA Chip Study In order to analyse the possibility that an extract according to the invention has an anti-age action, a DNA chip transcriptomic study has been made from human fibroblasts and melanised reconstituted human epidermis treated for 24 hours by two *Ipomoea batatas* root extracts comprising at least one DCQ DPG ester, that is a DCQ propane 1,3 diol ester according to the invention. The expression variations of the genes have been contextualised and biologically interpreted through the database "StratiCELL Skin Knowledge database".

4.1. Materials and Methods

Extracts

An *Ipomoea batatas* root extract, having a 3,5-DCQ concentration of 1.1±0.1 g/L respectively has been prepared by root exudation in DPG of *Ipomoea batatas* plant cultured above the ground (hereinafter extract no 2). 3,5-DCQ is the main compound of this extract (12-15 mass % of the total dry solid). This extract also comprises to a lesser proportion chlorogenic acid, DCQ DPG esters and other caffeic acid ester derivatives and their isomers. Thus, this is a mixture of compounds of the formula (I), wherein 3,5-DCQ is present with a vast majority. The solvent (DPG) content in v/v percentage is 70±5%, the extract pH is 3.0±0.1. In the example 4, this extract is entitled extract no 2.

An *Ipomoea batatas* root extract, having a DCQ propane 1,3 diol ester concentration of 1.3±0.3 g/L including 1.0±0.1 g/L 3,5-DCQ propane 1,3 diol ester, has been prepared by root exudation in biosourced propane 1,3 diol of *Ipomoea batatas* plant cultured above the ground (hereinafter extract no 1). The conversion of 3,5-DCQ into 3,5-DCQ propane 1,3 diol ester is higher than 95%. Thus, this extract also comprises to a lesser proportion chlorogenic acid, dicaffeoylquinic acids and their isomers. Thus, this is a mixture of compounds of the formula (I), wherein the 3,5-DCQ propane 1,3 diol ester is present with a vast majority. The solvent content is adjusted with water up to a v/v percentage of 55±5%, the extract pH is 4.2±0.2. In the example 4, this extract is entitled extract no 1.

Cell Culture

The first part of the study has been made on human dermis fibroblasts NHDFs (ATCC, CRL-2522, origin: foreskin) at about 40% of their proliferative potential in vitro. These cells have been cultured in single layer in DMEM medium (Invitrogen, 31885-049) containing antibiotics (penicillin/streptomycin, Invitrogen, 15140-122). These cells have been maintained in a wet atmosphere at 37° C. containing 5% $CO_2$.

The second part of the study has been made on reconstituted epidermis (StratiCELL®, RHE/MEL/001) containing primary human melanocytes NHEMs (Normal Human Epidermal Melanocytes) or not coming from a donor with a dark phototype (phototype IV to V) (Invitrogen, C2025C, batch no 439684). The tissues have been cultured at the air-liquid interface for 14 days in an appropriate culture medium, and a wet atmosphere at 37° C. containing 5% $CO_2$.

Determination of the Range of Study Concentrations of Both *Ipomoea batatas* Root Extracts by a Preliminary Cytotoxicity Study In order to determine the optimum analysis concentration for both extracts, a preliminary experiment has been made on fibroblasts NHDFs, on human melanocytes NHEMs and on reconstituted epidermis.

The fibroblasts NHDFs have been seeded in 24 well plates 24 hours before applying the extracts. The primary human melanocytes NHEM have been seeded in 24 well plates 24 hours before applying the extracts. The reconstituted epidermis (RHE/001; batch CB0314/2) has been transferred to a 12-well plate before being treated with the extracts.

Both extracts have been solubilised in the culture medium, and then placed in contact with the human fibroblasts NHDFs, the primary human melanocytes NHEMs, or epidermis differentiated during 24 hours.

This study consisted in evaluating the viability of cells and epidermis to MTS (3-(4,5-dimethythiazol-2-yl)-5-(3-carboxy-methoxyphenyl)-2-(4-sulfophenyl)-2H-tetrazolium) (Promega,G3581), 24 hours after adding both plant extracts and both solvents (DPG 70% pH=3 and propane 1,3 diol 56% pH=4.2), at 5 concentrations and 3 repeats (n=3) for the fibroblasts NHDFs and melanocytes NHEMs, and at 2 concentrations and 3 repeats (n=3) for the reconstituted epidermis.

SDS (sodium dodecyl sulphate) is toxic for cells and has been used as a positive control in order to validate the experiment.

At the end of this experiment, a non-cytotoxic concentration has been defined in order to conduct the transcriptomic analysis.

The following concentrations, in v/v percentage, have been tested:

Fibroblasts NHDFs and melanocytes NHEMs: 3%, 1%, 0.3% 0.1%, 0.03%

Reconstituted epidermis: 1% and 0.3%.

Cell Treatment

The extracts and solvents have been applied at a chosen concentration, for 24 h, in the culture medium of the fibroblasts NHDFs and the pigmented epidermis. Culture quadruplets have been made for each condition (n=4). At the end of the treatments, the populations of total RNAs have been extracted. The RNAs have been quantised by spectrophotometry (n=4) and their integrity has been analysed by capillary electrophoresis (for triplicates of each condition; n=3).

Extraction of Total RNA

The extraction of total RNAs has been made using the RNeasy kit (Qiagen). After 24 h treatment, the cells have been rinsed with PBS and lysed in ad hoc buffer, whereas the epidermis has been cut off the insert and directly dipped in this buffer.

The extraction and purification of the RNAs have been made according to the supplier's instructions. The total RNAs have then been preserved at −80° C. for the purpose of the transcriptomic analysis.

Qualification of the RNAs by Spectrophotometry and Capillary Electrophoresis

The concentration of the total RNAs has been determined by spectrophotometric measurement. The quality and integrity of the RNAs have then been checked by capillary electrophoresis (plate-form Agilent Bioanalyzer 2100-Agilent RNA 6000Nano Kit, 5067-1511).

Quantification of the RNAs by spectrophotometric measurement: an aliquot of each RNA has been diluted in RNAse-free water and its concentration has been determined using an Ultrospec 1100 Pro spectrophotometer (Amersham).

Integrity of the RNAs by capillary electrophoresis on Agilent Bioanalyzer: the integrity of the total RNA has been evaluated by viewing the peaks corresponding to the ribosomal RNAs. For the total RNAs of upper eukaryotes, the size of the ribosomal bands should be 1.9 kb for 18S-RNA and 4.7 kb for 28S-RNA. The intensity of the band corresponding to 28S-RNA should be higher than the intensity of the band corresponding to 18S-RNA (left profile hereinafter). Small diffuse bands representing RNAs with a lower molecular weight (RNAt and ribosomal RNA 5S) can be present. When the RNA is degraded, a spread of the bands of the ribosomal RNA as well as a noise of the RNAs with a higher molecular weight are observed.

Hybridisation Phase on GeneChip Human Gene 2.0 ST Chips (Affymetrix)

The RNAs have then been diluted at 50 ng/μL and 50 μL of each sample (n=3). The fourth replicate is used as a back-up.

The RNA samples (50 ng) have been amplified by the use of the Ribo-SPIA technology, according to 3 steps (Ovation Pico WTA System V2, NuGEN, 3302-2) and purified by the Agencourt RNA Clean up XP Beads (Agencourt-Beckam Coulter Genomics, A29168). For each sample, 4.5 μg have been fragmented and marked with biotin, within the NuGEN Encore Biotin Module (NuGEN, 4200-12). The hybridisation has been performed on DNA chips of the GeneChip Human Gene 2.0 ST model (Affymetrix, 902112). The steps of chip hybridisation, washing and fixing have been made according to the protocol defined by Affymetrix. The hybridisation solution has been prepared by the use of the Affymetrix Genechip Expression 3' Amplification Reagent Hybridisation Controls kits (Affymetrix, 900454) and Hybridisation Module for GeneChip Hybridisation, Wash and Stain Kit (Affymetrix, 900720), and mixed with the complementary DNA (DNAc) amplified in the previous steps. The hybridisation has been made for 18 h in the oven GeneChip Hybridisation Oven 640 (Affymetrix, 800139). Washing and revelation have been made using the GeneChip Fluidics Station 450 (Affymetrix, 00-0079) and the intensity measurements have been scanned with the GeneChip Scanner 3000 (Affymetrix).

Pre-treatment of the Hybridisation Data

The treatment of raw data has been made with the softwares R (v3.2.3; Ihaka and Gentleman, 1996) and the package "oligo" (v1.34.2; Carvalho BS and Irizarry AR, 2010) of the project BioConductor (v3.2; Gentleman et al, 2004). The last version of libraries provided by Affymetrix, built on the version 19 of the human genome (UCSC Human genome 19), and the method RMA, described by Irizarri et al. (Irizarri et al, 2003a; Irizarri et al, 2003b) have been used in order to guide and perform the pre-treatment and annotation of the sequences.

Data Analysis, Annotation and Thematic Analysis

The individual statistical analysis of the genes/transcripts has been made with the methods "Moderated t" and "Moderated F" implemented in the package R Limma 3.26.8 (Smyth GK, 2004).

The annotation of genes and definition of gene groups for the over-representation analysis have been made first based on internal data "StratiCELL Skin Knowledge Database" (Salmon M & Berger F, 2014).

The over-representation analysis has been made with the hypergeometric test method for the purpose of characterising the factors themes/groups of dermo-cosmetic interest at the beginning of their detected and differentially expressed targets. The analysis has been conducted at the beginning of the list of the genes detected with a p-value of 0.05 and an expression level difference (fold-change or FC) higher than 1.5 (bilateral).

4.2, Results

Determination of the Analysis Concentration of Both *Ipomoea batatas* Root Extracts by a Preliminary Cytotoxicity Study A cytotoxicity study has been made on fibroblasts NHDFs and on rebuilt epidermis as well as on human primary melanocytes NHEMs in order to exclude a possible specific cytotoxicity on these cells, present in a small number within the rebuilt epidermis. The respective extracts and solvents used for the preparation thereof, have been applied to the culture media, for 24 h (n=3). The untreated control has been arbitrarily set to 100% viability and the cytotoxicity threshold has been set conventionally to 80% viability. The SDS condition is the positive control which validates the experiment.

Based on the results of the preliminary cytotoxicity study (data not shown), the optimum concentrations (in v/v percentage) selected for each of both extracts and solvents are the following ones:

Extract 1 and propane 1,3-diol: for 3% fibroblasts NHDFs and for melanocytes NHEMs as well as for 0.3% reconstituted epidermis.

Extract 2 and DPG: for 3% fibroblasts NHDFs and for melanocyte NHEMs as well as for 0.3% reconstituted epidermis.

Quantification of the RNAs by Spectrophotometry

The absorbance ratio at 260 nm and 280 nm is used to evaluate the RNA purity. A ratio close to 2 enables the sample to be considered as being pure and free of contamination by proteins. The ratio 260/230 is used as a secondary measurement of the sample purity. The value 260/230 is generally higher than the ratio 260/280 and is expected at around 2.2. The ratios obtained for all the samples of the present study are thus satisfactory (data not shown) and have been qualified then by capillary electrophoresis.

Qualification of the RNAs by Capillary Electrophoresis

The different RNA populations do show the presence of narrow peaks, corresponding to the ribosomal RNAs 18S and 28S, and a balanced ratio between both peaks. The absence of intermediate and spread peaks, characteristics of RNA degradation products is a mark of the integrity of the different populations (data not shown).

The quality and integrity of the extracted RNAs being demonstrated, hence they can be used for continuing the protocol and committed in amplification, purification, marking with biotin and then hybridisation on DNA chips reactions.

Analysis of the Expression Modifications of Genes Induced by the Extract no 2

1) Effects of the Extract no 2 on the Transcriptome of Human Dermis Fibroblasts NHDFs.

The extract no 2 has been added to the culture medium of fibroblasts NHDFs (n=4) at a 3% v/v concentration. A control only treated by the 70% DPG solvent (extract vehicle, 3% v/v concentration, n=4) has also been analysed. After 24 h culture of the fibroblasts NHDFs, the gene expression differences have been analysed by DNA chip hybridisation.

Some significant results are summarised as a table (Table 5) indicating genes representative of a beneficial cosmetic effect, significantly varying, 24 h after applying the extract no 2 on human dermis fibroblasts NHDFs.

| p-value | Fold change (FC) | Symbol | Name |
|---|---|---|---|
| 1.0e−6 | 2.8 | HMOX1 | heme oxygenase-1 |
| 6.4e−5 | 3.02 | MT1G/ MT1K | metallothionein 1G/ metallothionein 1K |
| 5.2e−4 | 1.45 | FTH1 | ferritin, |
| 1.5e−2 | 1.22 | NQO1 | NAD(P)H dehydrogenase quinone 1 |
| 2.3e−2 | 1.69 | MT1H | metallothionein 1H |

Table 5: Examples of genes which significantly vary 24 h after applying the root extract no 2 (3%) on human dermis fibroblasts NHDFs. The symbol of the genes, the name of the genes, the expression fold change (FC) with respect to the 70% DPG vehicle (3%) (FC>1: increase—FC<1: decrease) and the p value are presented.

The extract no 2 induces the overexpression of metallothioneins 1G (MT1G) and 1H (MT1H) known for their detoxifying and anti-radical activity. Metallothioneins (MT) are proteins with a low molecular weight (6-10 kDa), containing many cysteine residues, and two heavy metal chelation domains. They can be activated by different stimuli, such as heavy metals, UV, inflammatory cytokines or even some growth factors. The MTs play a crucial role in maintaining the homeostasis of physiological metals and detoxification of toxic metals from urban pollution, such as copper, nickel, mercury or cadmium. They are also widely involved in the protection against oxidative stress, in particular at the mitochondria level where their presence is finely regulated by the breathing related stress level.

Consistently with the previous examples 1 to 3, the extract no 2 induces an increase in the expression of the HMOX and NQO1 genes. The HMOX1 gene codes for heme oxygenase (HO-1) which is involved in heme degradation and is well known for its protective role against oxidative stress. Its protective role is essentially due to its capacity to degrade heme, having pro-oxidant properties into ions Fe2+, carbon monoxide and biliverdin, a precursor of a strong antioxidant metabolite, bilirubin. NAD(P)H dehydrogenase, quinone 1 (NQO1) is a cytosolic flavoprotein under the control of the transcription factor RNF-2. NQO1 promotes, by reducing hydroquinone formation from quinones, preventing radical species from being produced. NQO1 is overexpressed after contact with pro-oxidant agents and heavy metals, after exposure to UVs or ionising radiations, in order to protect the cell from their deleterious effects.

Thus, a stimulation of the gene coding for the ferritin (FTH1) heavy chain is observed. This is often overexpressed as a result of an exposure to a radical stress. It is responsible for iron storage, coming from heme degradation, in a non-harmful form and participates in transport and regulation of its availability depending on circumstances. Indeed, iron catalyses many beneficial reactions but also harmful reactions as lipid peroxidation and Fenton reaction producing hydroxyl radicals.

2) Effects of the Extract no 2 on the Transcriptome of Melanised Reconstituted Human Epidermis.

The extract no 2 has been added in the culture medium in melanised epidermis (n=4) at a 0.3% v/v concentration. A control only treated by 70% DPG solvent (extract vehicle, 0.3% v/v concentration, n=4) has also been analysed. After 24 h culture of the melanised epidermis, the gene expression differences have been analysed by DNA chip hybridisation.

Some significant results are summarised as a table (Table 6) indicating genes representative of a beneficial cosmetic effect, significantly varying, 24 h after applying the extract no 2 on melanised human epidermis.

TABLE 6

Examples of genes which significantly vary 24 h after applying the root extract n° 2 (3%) on melanised human epidermis. The symbol of the genes, the name of the genes, expression fold change (FC) with respect to the 70% DPG vehicle (3%) (FC >1: increase-FC <1: decrease) and the p value are presented.

| p-value | Fold change (FC) | Symbol | Name |
|---|---|---|---|
| 2.9e−8 | −6.3 | SDC2 | syndecan proteoglycan 2 |
| 1.3e−6 | −8.74 | FGF2 | growth factor 2 of fibroblasts |
| 2.8e−6 | −4.84 | FGF7/KGF | growth factor 7 of fibroblasts |
| 3.5e−4 | 1.72 | CALML3 | calmodulin-like protein 3 |
| 5.5e−3 | −1.62 | PAX3 | transcription factor paired box 3 |
| 2.0e−3 | 1.69 | PDE7A | Phosphodiesterase 7A |
| 2.9e−5 | 2.22 | LAMC2 | laminin gamma 2 |
| 1.3e−4 | 1.71 | LAMA3 | laminin alpha 3 |
| 1.6e−3 | 1.6 | LAMB3 | laminin beta 3 |

The extract no 2 induces several expression variations of key genes involved in skin pigmentation and stimulates the expression of the three sub-units α3, β3 and γ2 of the laminin 5, a major component of the basement membrane.

Skin Pigmentation:

The genes coding for phosphodiesterase 7A (PDE7A) and for calmodulin-like protein-3 (CALML3) involved in the regulation of the intracellular concentration of cyclic adenosine monophosphate (3'5'AMPc), the second essential messenger produced as a result of the activation by α-MSH of adenylate cyclase and required to stimulate protein kinase A (PKA) downstream of the pathway, leading to the expression of the transcription factor MITF, to the expression of tyrosinase and to melanin synthesis, are positively modulated.

PDE7A is part of the phosphodiesterase family regulating cyclic AMP intracellular production through its hydrolysis into its inactive 5'AMP form, hence negatively regulating the signalling pathway α-MSH/MC1R.

Further, the phosphodiesterases can be active by Ca2+/calmodulin (CM) complexes. The process starts with bonding Ca2+ ions to calmodulin and to calmodulin-like proteins (CALM) generating an active conformation. The active form is then associated with phoshodiesterases with an enzyme activation.

The overexpression of calmodulin-like protein-3 could thus enhance phosphodiesterase activity, limit the α-MSH/MC1R pathway and melanin synthesis.

The gene coding for the growth factor KGF/FGF-7 is widely underexpressed. It has been demonstrated that KGF/FGF-7 promotes melanosome transfer through the activation of its specific receptor present at the surface of the neighbouring keratinocytes (FGFR2b/KGFR), and stimulating the melanosome phagocytosis process. Further, the growth factor KGF/FGF-7 is actually described as an initiation factor for hyper-pigmentary injuries as solar lentigo or melasma.

By strongly limiting the presence of KGF/FGF-7, the extract no 2 is an excellent candidate for treating and/or preventing this type of injuries characterised by a localised hyperpigmentation (pigmentary spots).

The extract no 2 strongly represses the expression of the gene coding for the proteoglycan Syndecan-2. The SDC2 gene silencing by a specific siRNA is associated with a reduction in the melanin synthesis, whereas its overexpression induces the reverse effect. In addition, the SDC2 expression is increased as a result of a UVB exposure, and this increase is required to observe an induction of melanin synthesis under these conditions.

Finally, a decrease in the gene coding for the transcription factor Paired Box 3 (PAX3), as well a decrease in the gene coding for the fibroblast growth factor (FGF2), well documented for its melanocyte viability regulating role through the PAX3 STAT3-dependent expression are observed. An expression decrease of the FGF2 gene is thus logically related to a repression of PAX3 gene.

All these data highlight a possible modulating effect of the extract no 2 of the epidermis pigmentation.

Elasticity and Mechanical Strength of Skin:

The basement membrane (BM) mechanically supports the epidermis, maintains contact and exchanges between the same and the subjacent dermis, and provides a barrier and selective filter function. During the skin aging, a flattening and a thinning of the BM is observed. This flattening will widen furrows of the surface microdepression network (network of more or less deep furrows which dig the epidermis surface), and fine lines that will appear. The basement membrane thus is a main target for an anti-age strategy.

The joint induction of the three laminin 5 sub-units, that is laminin α3 (LAMA3), laminin β3 (LAMB3) as well as laminin γ2 (LAMC2) is quite remarkably observed. Laminin 5 or laminin 332, consisting of the three sub-units α3, β3 and γ2, plays an essential role within the BM. Via its interaction with integrins, it ensures anchorage of epidermis keratinocytes to the dermis fibres, in order to form a complex network which provides mechanical support.

Analysis of the Expression Modifications of Genes Induced by the Extract no 1

1) Effects of the Extract no 1 on the Transcriptome of Human Dermis Fibroblasts NHDFs.

The extract no 1 has been added in the culture medium of fibroblasts NHDFs (n=4) at a 3% v/v concentration. A control only treated by solvent 56% propane 1,3 diol (extract vehicle, 3% v/v concentration, n=4) has also been analysed. After 24 h culture of the fibroblasts NHDFs, the gene expression differences have been analysed by DNA chip hybridisation.

Some significant results are summarised as a table (Table 7) indicating genes representative of a beneficial cosmetic effect, significantly varying 24 h after applying the extract on human dermis fibroblasts NHDFs.

TABLE 7

Examples of genes which significantly vary 24 h after applying the root extract n° 1 (3%) on human dermis fibroblasts NHDFs. The symbol of the genes, the name of genes, expression fold change (FC) with respect to the 70% DPG vehicle (3%) (FC >1: increase-FC <1: decrease) and the p-value are presented.

| p-value | Fold change (FC) | Symbol | Name |
|---|---|---|---|
| 4.7e−4 | −1.59 | FGF7/KGF | growth factor 7 of fibroblasts/growth factor keratinocyte |
| 3.9e−3 | −1.33 | KITLG/SCF | KIT ligand or factor of stem cells |
| 1.0e−2 | −1.44 | HGF | growth hepatocyte factor |

Skin Pigmentation:

It is now well demonstrated that signals emitted by the dermis fibroblasts strongly influence skin pigmentation.

In addition, in some skin pathologies reflected in a local hyperpigmentation, such as scleroderma, "café-au-lait" macules of neurofibromatosis or even solar lentigo, an increase in pro-melanogenic growth factors has been observed within the dermal compartment. These factors have been identified as "stem cell factor" (SCF or Kit ligand), "hepatocyte growth factor" (HGF) and "keratinocyte growth factor" (KGF/FGF-7). Further, as has been previously discussed for the extract no 2, KGF/FGF-7 promotes melanosome transfer through the activation of its receptor present at the keratinocyte surface, stimulating melanosome phagocytosis process and tissue pigmentation. Remarkably, the extract no 1 inhibits the expression of these three factors simultaneously (Table 7).

2) Effects of the Extract no 1 on the Transcriptome of Melanised and Reconstituted Human Epidermis.

The extract no 1 has been added in the culture medium of melanised epidermis (n=4) at a 0.3% v/v concentration. A control only treated by the solvent 56% propane 1,3 diol (extract vehicle, 0.3% v/v concentration, n=4) has also been analysed. After 24 h culture of the melanised epidermis, the gene expression differences have been analysed by DNA chip hybridisation.

Some significant results are summarised as a table (Table 8) indicating genes representative of a beneficial cosmetic effect, significantly varying 24 h after applying the extract on melanised human epidermis.

TABLE 8

Examples of genes which significantly vary 24 h after applying the root extracting n° 1 (3%) on melanised human epidermis. The symbol of the genes, the name of genes, expression fold change (FC) with respect to the vehicle, 56% 1,3 propane diol solvent (at 0.3%) (FC >1: increase-FC <1: decrease) and the p-value are presented.

| p-value | Fold change (FC) | Symbol | Name |
|---|---|---|---|
| 3.0e−2 | 1.28 | CALML3 | calmodulin-like protein 3 |
| 5.3e−4 | 1.5 | PDE7A | phosphodiesterase 7A |
| 8.2e−6 | −2.22 | KIF20A | kinesin family member 20A |
| 1.5e−4 | −1.73 | KIF15 | kinesin family member 15 |

TABLE 8-continued

Examples of genes which significantly vary 24 h after applying the root extracting n° 1 (3%) on melanised human epidermis. The symbol of the genes, the name of genes, expression fold change (FC) with respect to the vehicle, 56% 1,3 propane diol solvent (at 0.3%) (FC >1: increase-FC <1: decrease) and the p-value are presented.

| p-value | Fold change (FC) | Symbol | Name |
|---|---|---|---|
| 1.3e−3 | −1.82 | KIF11 | kinesin family member 11 |
| 4.3e−3 | −1.57 | KIF24 | kinesin family member 24 |
| 4.6e−3 | −1.59 | KIF18A | kinesin family member 18A |
| 1.1e−2 | −1.52 | KIF14 | kinesin family member 14 |
| 1.2e−2 | −1.58 | KIF23 | kinesin family member 23 |
| 1.5e−5 | 2.28 | LAMC2 | laminin gamma 2 |
| 1.4e−4 | 1.62 | LAMA3 | laminin alpha 3 |
| 1.2e−3 | 1.61 | LAMB3 | laminin beta 3 |

The extract no 1 induces several expression variations of key genes involved in skin pigmentation and stimulates the expression of the three sub-units α3, β3 and γ2 of the laminin 5, a major component of the basement membrane.

Skin Pigmentation:

As for the extract no 2, an overexpression of two genes, that is phosphodiesterase 7B (PDE7A) and calmodulin-like protein-3 (CALML3), involved in the AMPc phosphodiesterase (PDE) activity, modulating the intracellular concentration of cyclic adenosine monophosphate (3'S'AMPc), the second messenger produced as a result of the activation of adenylate cyclase by α-MSH is observed. A decrease in the AMPc intracellular concentration could result in a decrease in melanin synthesis.

In parallel, an underexpression of several members of the kinesin family (KIF genes), motor proteins involved in melanosome transport to the end of the melanocyte dendrites is observed. Melanosomes make up melanocyte-specific intracellular organites, within which melanin is synthesised and stored. It is now well established that melanosome transfer inhibition is a strategy for designing a depigmenting active.

It has been demonstrated that kinesins are inactivated when the concentration of AMPc drops, causing a melanosome aggregation in cells. The joint decrease in the expression of multiple kinesins could thus be a consequence of a drop in the concentration of AMPc following a stimulation by the extract no 1 of the phosphodiesterase activity.

The expression decrease and supposedly the anterograde transport activity of melanosomes via kinesins, promoting the aggregation thereof and inhibiting transfer thereof, thus underlies our depigmenting effect hypothesised of the extract no 1.

A decrease in KGF/FGF-7 production by fibroblasts (Table 7) enhances this hypothesis, the latter being indeed a key element required for the activation of the melanosome phagocytosis process via the tyrosine kinase FGFR2b/KGFR receptor during the transfer process.

Thus, the extract no 1 could thereby be the base of a depigmenting allegation and an original strategy enabling pigmentary spots appearing with age (solar lentigo) to be mitigated, which are characterised by a local hyperpigmentation through an original mechanism based on the regulation of the paracrine communication between the dermal and epidermal behaviour aiming at stimulating melanogenesis.

In addition, both extracts have complementary effects with respect to a possible depigmenting allegation. Indeed, the extract no 2 acts on several melanogenic factors at the epidermis (melanocytes and keratinocytes), whereas the extract no 1 remarkably acts at the dermis fibroblasts on the 3 growth factors known to act in a paracrine way on the melanocytes and keratinocytes of epidermis and involved in the appearance of age-related pigmentary spots.

Both this complementary and the joint action on the same targets suggest an obvious interest to develop a strategy aiming at combining both extracts, so as to enhance expected effects.

Elasticity and mechanical resistance of skin:

As for the extract no 2, the joint induction of the three laminin 5 sub-units, that is laminin α3, laminin β3) as well as laminin γ2 (Table 8) is observed in the same proportions.

Thus, both extracts could hence be the base of an anti-age allegation by enabling loss of skin elasticity and mechanical strength to be mitigated.

4.3. Conclusion

The transcriptomic study described in the present example shows the significant modification of the expression of genes involved in an oxidative stress in human fibroblast cell culture in response to the application of the extract no 2, and thus illustrates the protective role of DCQ DPG esters against this oxidative stress.

Also, as shown in the present example, the DCQ DPG esters and DCQ propane 1,3 diol esters present in the extract no 2 and the extract no 1 respectively have significantly modified the expression of genes involved in skin pigmentation and basement membrane in cultures of melanised reconstituted human epidermis. Thus, both extracts used alone or in combination for a complementary or even synergistic effect, could thereby be the base of an anti-age allegation.

BIBLIOGRAPHY

Benilton S Carvalho and Rafael A Irizarry. Bioinformatics 2010 (Oxford University Press), 26:19, Pp 2363-7, Doi: 10.1093/Bioinformatics/Btq431. Buckley & Klaassen, 2009
D. Gems, L. Partridge. Cell Metabolism, 2008, 7: 200-204
F. J. Kelly. Occup. Environ. Med., 2003, 60: 612-616
Gentleman R, Carey Vj, Bates Dm, Bolstad B, Dettling M, Dudoit S, Ellis B, Gautier L, Ge Y. Genome Biology 2004, 5, R80
Ihaka R and Gentleman T. Journal Of Computational And Graphical Statistics 1996, 5 (3), 299-314
Irizarry Ra, Hobbs B, Collin F, Beazer-Barclay Yd, Antonellis Kj, Scherf U, Speed Tp. Biostatistics. 2003b, 4 (2), 249-64
Irizarry Ra, Ooi S I, Wu Z, Boeke Jd. Stat Appl Genet Mol Biol. 2003a, 2, Epub. 2003 Mar. 18
Kevin C. Kregel, Hannah J. Zhang. Am J Physiol Regul Integr Comp Physiol, 2007, 292:R18-R36
Lima et al., Mol. Nutr. Food Res., 54, 1-13, 2010; Calabrese et al., Clinics in Dermatology, 26, 358-363, 2008
Lu et al., 2009; Strange et al., 2001
Morse and Choi, 2005; Vile et al., 1994)
Murphy, 2013
Nguyen et al., 2009
Petri et al., 2012
Salmon M & Berger F. Expression Cosmétique 2014, 30, 91-94
S. I. Rattan. Ann. N. Y. Acad. Sci. 1998, 854: 54-60
Smyth Gk. Statistical Applications In Genetics And Molecular Biology 2004, 3 (3)
Suresh I. S. Rattan. The Journals of Gerontology Series A: Biological Sciences and Medical Sciences, 2004, 59:B705-B709
US 2004/0170581
WO 01/33942
Zsolt Radak, Hae Young Chung, Sataro Goto. Biogerontology, 2005, 6: 71-75

The invention claimed is:

1. A compound of general formula (I)

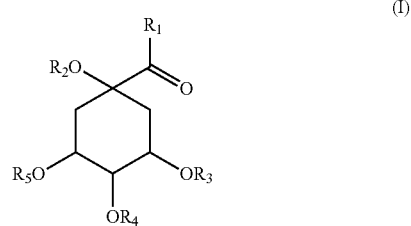

wherein $R_1$ represents a radical chosen from the group consisting of the radicals of the following formulae (IIa) to (IIe), (III), (IVa) to (IVb) and (Va) to (Vd):

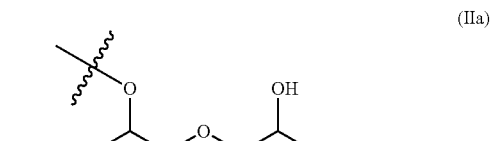

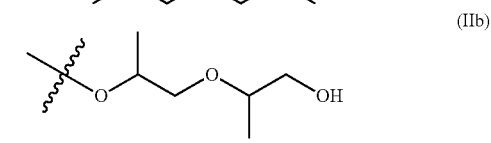

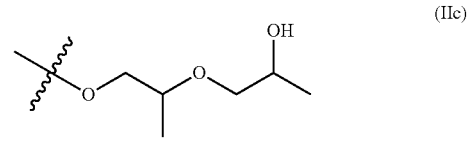

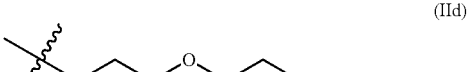

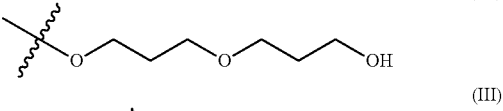

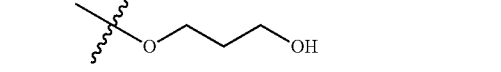

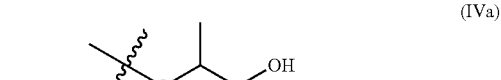

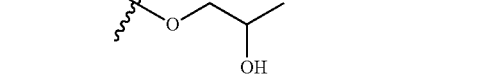

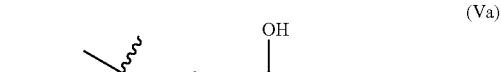

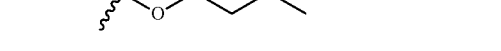

(Vb)
(Vc)
(Vd)

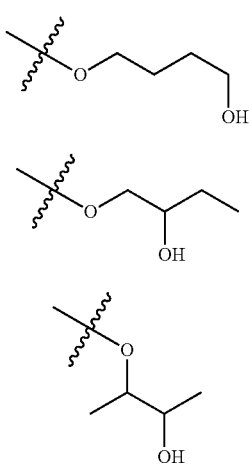

and wherein any two of the radicals $R_2$, $R_3$, $R_4$ and $R_5$ represent a caffeoyl group, the other two representing a hydrogen atom.

2. A compound according to claim 1, wherein $R_2$ represents a hydrogen atom.

3. A compound according to claim 1, wherein $R_2$ and $R_4$ represent a hydrogen atom.

4. A compound according to claim 1, said compounds being selected from the molecules of the following respective formulae (Ia), (Ib), (Ic), (Id), (Ie), (If), (Ig), (Ih), (Ii), (Ij), (Ik) and (Il):

(Ia)

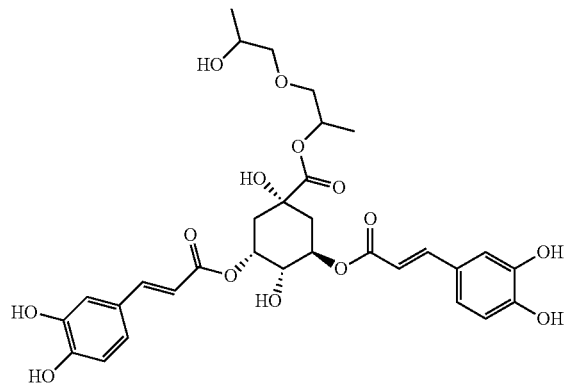

(Ib)

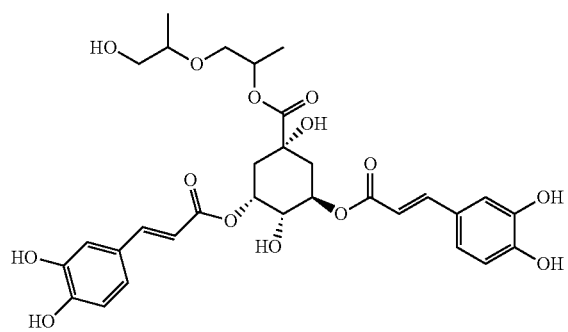

(Ic)

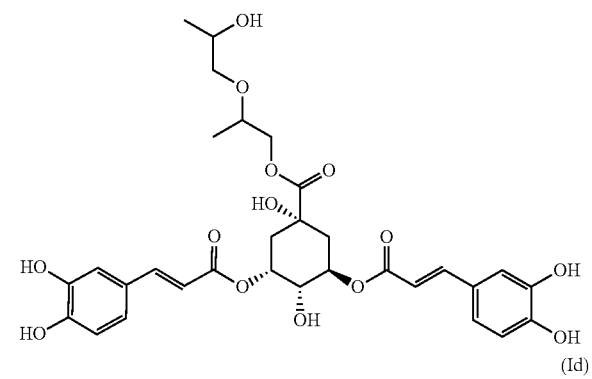

(Id)

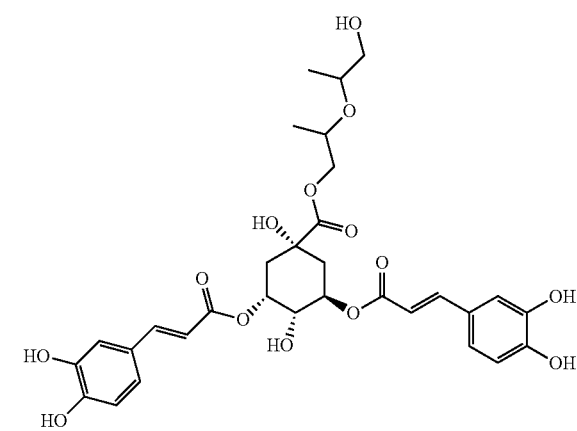

(Ie)

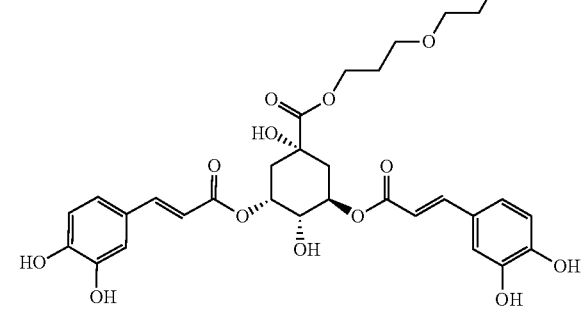

(If)

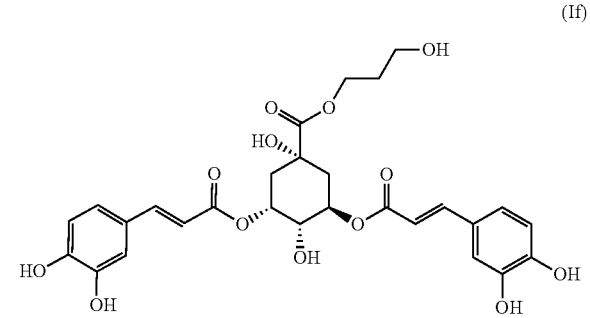

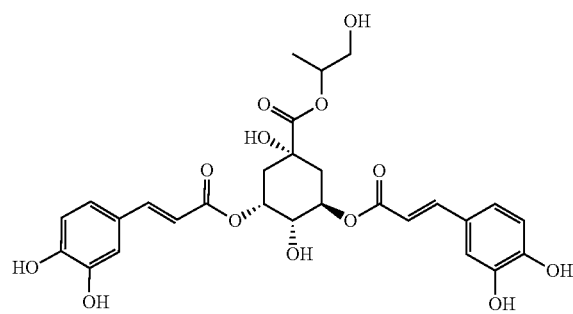
(Ig)
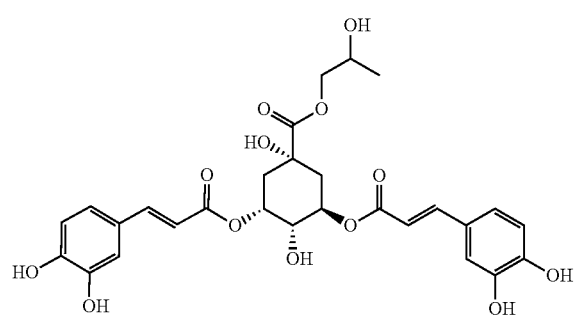
(Ih)
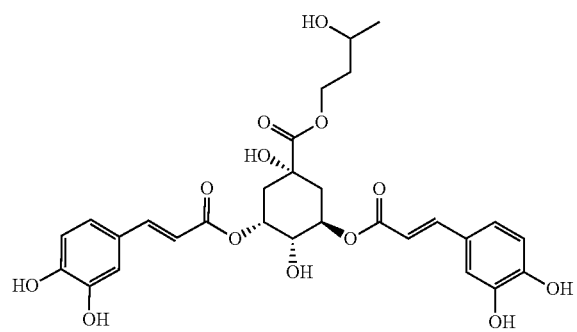
(Ii)
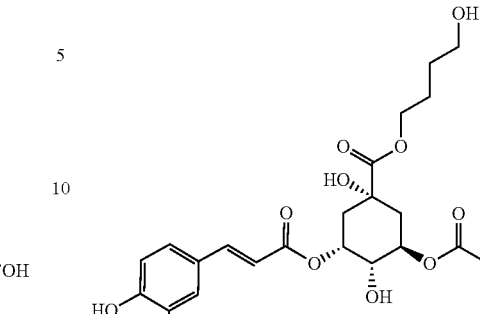
(Ij)
(Ik)
(Il)
5. A cosmetic composition comprising as an active agent at least one compound according to claim 1.
* * * * *